United States Patent [19]
Afonso et al.

[11] Patent Number: 5,942,522
[45] Date of Patent: *Aug. 24, 1999

[54] ANTIVIRAL COMPOUNDS AND ANTIHYPERTENSIVE COMPOUNDS

[75] Inventors: Adriano Afonso, West Caldwell; Jay Weinstein, Upper Montclair; Margaret Jevnik Gentles, Bloomfield, all of N.J.

[73] Assignee: Schering Corporation, Kenilworth, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/806,585

[22] Filed: Feb. 26, 1997

Related U.S. Application Data

[62] Continuation of application No. 08/382,740, Feb. 2, 1995, abandoned, which is a division of application No. 08/030,186, Mar. 1, 1993, Pat. No. 5,412,104, filed as application No. PCT/US91/06252, Sep. 6, 1991, which is a continuation-in-part of application No. 07/579,420, Sep. 7, 1990, abandoned, application No. 07/579,749, Sep. 7, 1990, abandoned, and application No. 07/664,272, Mar. 4, 1991, abandoned.

[51] Int. Cl.$^6$ .......................... A61K 31/37; C07D 215/22
[52] U.S. Cl. ............................................. 514/312; 546/155
[58] Field of Search .............................. 514/312; 546/14, 546/23, 155

[56] References Cited

U.S. PATENT DOCUMENTS

| | | | |
|---|---|---|---|
| 2,646,355 | 7/1953 | Zweifel et al. | 549/288 |
| 2,844,594 | 7/1958 | Long et al. | 549/288 |
| 3,008,969 | 11/1961 | Pretka | 549/288 |
| 3,025,299 | 3/1962 | Pfister et al. | 546/155 |
| 3,141,893 | 7/1964 | Pfister et al. | 549/288 |
| 3,275,658 | 9/1966 | Lednicer | 548/525 |
| 3,449,335 | 6/1969 | Copeland | 546/155 |
| 3,515,721 | 6/1970 | Ritter et al. | 549/288 |
| 3,715,360 | 2/1973 | Gaeng et al. | 546/155 |
| 3,960,868 | 6/1976 | Ferrini et al. | 546/156 |
| 4,024,275 | 5/1977 | Archer . | |
| 4,031,099 | 6/1977 | Buckle et al. | 546/155 |
| 4,066,651 | 1/1978 | Brittain et al. | 546/157 |
| 4,079,066 | 3/1978 | Gardner | 560/250 |
| 4,107,310 | 8/1978 | Allais et al. | 546/156 |
| 4,124,587 | 11/1978 | Hardtmann | 546/155 |
| 4,138,490 | 2/1979 | Brittain et al. | 546/157 |
| 4,168,312 | 9/1979 | Schacht et al. | 546/155 |
| 4,187,309 | 2/1980 | Hardtmann | 546/155 |
| 4,187,310 | 2/1980 | Brittain et al. | 546/157 |

(List continued on next page.)

FOREIGN PATENT DOCUMENTS

| | | |
|---|---|---|
| 0059698 | 9/1982 | European Pat. Off. . |
| 59698 | 9/1982 | European Pat. Off. . |
| 0385630 | 9/1990 | European Pat. Off. . |
| 269 382 | 6/1989 | Germany . |
| 44-16373 | 7/1969 | Japan . |
| 59-59683 | 4/1984 | Japan . |
| 62-240677 | 10/1987 | Japan . |
| 63-290821 | 11/1988 | Japan . |
| 63-295561 | 12/1988 | Japan . |
| 1505941 | 9/1989 | Russian Federation . |
| 578536 | 8/1976 | Switzerland . |
| 197809 | 9/1978 | United Kingdom . |
| 92-04326 | 3/1992 | WIPO . |
| 92-04327 | 3/1992 | WIPO . |
| 92-04328 | 3/1992 | WIPO . |

OTHER PUBLICATIONS

Knierzinger et al., J. Heterocyclic Chem. 17, pp. 225–229, (1980).
Primafiore, Chem. Abstr vol. 88 entry 3769 (1976).
Primafiore et al, Atti Accad. Sci. 1st Bologna CI Sci Fis Rend 3(2), 95–98 (1976).
CA, vol. 114, 1991, Srivasta et al entry 143242P.
CA, vol. 86, 1977, Minker et al, 26053v.
J. Chem. Soc. 438–455 (1964) Clark and Gundon.
CA 88(5): 36830b (1978).
Yoshizaki et al., CA, vol. 113: 211864z (1990).
Schaefer et al., CA, vol. 109: 170249z (1988).
Derwent Abstract No. 81–35421D/198120 for J90005–752–B; published Feb. 1990.
Derwent Abstract No. 82–12633E/198207 for J89035–827–B; published Jul. 1989.
Primafiore et al., Atti. Accad. Sci. 1st Bologna CL Sci Fis Rend 3(2), 95–98 (1976) (CA 88(5)): 37696Z attached).
J. Chem. Soc. Perkin Trans., vol. 9 Sept., 1989, Brownsart et al., 1679–1686.
J. Chem. Soc. Perkin; vol. 5 May, 1989, Gaston et al., 905–908.
J. Med Chem. 1985, 28, 748–752 (Diana et al.).
CA 114: 143242P (1991) (Srivastava et al.).
CA 86:26053v (1977) (Minker et al.).
Briet et al., Chem. Abstract vol. 87, entry 184369c (1977).

*Primary Examiner*—Donald G. Daus
*Attorney, Agent, or Firm*—Henry C. Jeanette

[57] ABSTRACT

Compounds useful as antihypertensive agents and useful as antiviral agents against DNA-containing viruses, such as herpes group viruses, are disclosed. The compounds are represented by Formula 1.0:

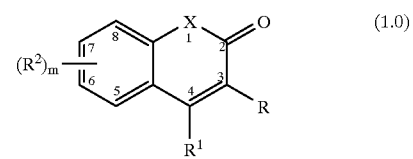

and their pharmaceutically acceptable salts and solvates.

Pharmaceutical compositions containing compounds represented by Formula 1.0 are disclosed. Methods of treating a viral infection using compounds represented by Formula 1.0 are disclosed. Also disclosed are methods of treating hypertension using compounds of Formula 1.0 wherein R is selected from the group consisting of H, halogen and —C(O)OR$^6$; and R$^1$ is selected from the group consisting of —OR$^{14}$, —O(CH$_2$)$_a$C(H)$_{3-i}$Z$_i$ and —O(CH$_2$)$_n$N(R$^{15}$)$_2$.

8 Claims, No Drawings

U.S. PATENT DOCUMENTS

| | | | |
|---|---|---|---|
| 4,190,659 | 2/1980 | Hardtmann | 546/155 |
| 4,218,448 | 8/1980 | Aldrich et al. | 546/157 |
| 4,251,659 | 2/1981 | Aldrich et al. | 546/166 |
| 4,271,303 | 6/1981 | Vamvakaris et al. | 546/155 |
| 4,281,131 | 7/1981 | Hardtmann et al. | 546/156 |
| 4,284,768 | 8/1981 | Santilli | 546/156 |
| 4,363,811 | 12/1982 | Evans et al. | 549/399 |
| 4,526,894 | 7/1985 | Enomoto et al. | 514/312 |
| 4,547,511 | 10/1985 | Eriksoo et al. | 514/312 |
| 4,607,039 | 8/1986 | Le Count et al. | 546/155 |
| 4,710,507 | 12/1987 | Campbell et al. | 514/312 |
| 4,902,693 | 2/1990 | Blythin et al. | 514/300 |
| 4,954,518 | 9/1990 | Takano et al. | 514/456 |
| 4,963,655 | 10/1990 | Kinder et al. | 549/213 |
| 5,064,756 | 11/1991 | Carr et al. | 435/32 |
| 5,175,151 | 12/1992 | Afonso et al. | 514/312 |
| 5,179,093 | 1/1993 | Afonso et al. | 514/312 |
| 5,179,107 | 1/1993 | Afonso et al. | 514/312 |
| 5,190,956 | 3/1993 | Afonso et al. | 514/312 |
| 5,250,547 | 10/1993 | Lochead et al. | 514/337 |
| 5,378,694 | 1/1995 | Afonso et al. | 514/312 |
| 5,382,572 | 1/1995 | Afonso et al. | 546/312 |
| 5,412,104 | 5/1995 | Afonso et al. | 514/63 |
| 5,614,532 | 3/1997 | Caruna | 514/312 |
| 5,696,241 | 12/1997 | de Crous | 546/155 |

ANTIVIRAL COMPOUNDS AND ANTIHYPERTENSIVE COMPOUNDS

This application is a continuation of U.S. application Ser. No. 08/382,740, filed Feb. 2, 1995, now abandoned, which application in turn is a division of U.S. application Ser. No. 08/030,186, filed Mar. 1, 1993, now U.S. Pat. No. 5,412,104, which in turn is the U.S. national application corresponding to International Application No. PCT/US91/06252 filed Sep. 6, 1991 and designating the United States, which PCT application is in turn a continuation-in-part of U.S. application Ser. No. 07/579,420, filed Sep. 7, 1990, now abandoned, U.S. application Ser. No. 07/579,749, filed Sep. 7, 1990, now abandoned and U.S. application Ser. No. 07/664,272, filed Mar. 4, 1991 now abandoned.

BACKGROUND

This invention relates to compounds having antiviral activity and to compounds having antihypertensive activity, pharmaceutical compositions containing them, and methods of treatment utilizing the compositions. In particular, this invention is related to compounds having antiviral activity against viruses of the herpes group, pharmaceutical compositions containing the compounds, and methods of treating infections with viruses of the herpes group using the pharmaceutical compositions.

There are four separate viruses of the herpes group which infect and cause disease in humans. These are (1) herpes simplex virus 1 and 2 (HSV-1 and HSV-2, respectively); (2) cytomegalovirus (CMV); (3) varicella-zoster virus (VZ); and (4) Epstein-Barr virus (EB). Examples of diseases associated with herpes simplex virus infection include herpes labialis, genital herpes (herpes progenitalis), neonatal herpes, herpetic keratitis, eczema herpeticum, disseminated herpes, occupational herpes, herpetic gingivostomatitis, meningitis (aseptic), and encephalitis.

CMV is widespread in humans and numerous other mammals. The great majority of human CMV infections are subclinical; that is, the primary infection occurs with no signs or symptoms. An exception to this is a congenital infection which occasionally gives rise to cytomegalic inclusion body disease in infants. There is also a mononucleosis-like syndrome caused by the virus.

The great majority of serious cases due to CMV infection come from recurring infections in immuno-compromised patients, such as transplant patients and cancer patients. It has been estimated that silent CMV infections have occurred in a majority of humans by the time adulthood is reached.

VZ virus is associated with chicken-pox (varicella) and shingles (zoster) in humans.

EB virus is quite common and causes glandular fever; it is also believed to be responsible for genetic damage that leads to Burkitt's lymphoma.

Examples of drugs used to treat herpes infections include: (1) IUDR (5'-iodo-2'-deoxyuridine); (2) Ara-C (1-[beta-D-arabinofuranosyl]-cytosine); (3) Ara-A (9-beta-D-arabinofuranosyladenine); and (4) Acyclovir (9-[(2-hydroxyethoxy)methyl]guanine). Also Haines et al. (U.S. Pat. No. 4,757,088 issued Jul. 12, 1988) disclose that lidocaine (2-(diethylamino)-N-(2,6-dimethylphenyl) acetamide) is an antiviral agent in cell culture against HSV-1 and HSV-2, and is able to treat herpes virus infections of mammals. Haines et al. also disclose that lidocaine is particularly effective in the treatment of HSV oral and genital lesions in humans. According to Haines et al., the addition of pantothenic acid or its alcohol and salt forms, dexpanthenol and pantothenate respectively, to lidocaine or lidocaine hydrochloride significantly enhances the antiviral activity of those drugs.

Human hypertension is a disease of multiple etiologies. Drugs that act to control one form may not be effective in controlling another. Therefore, further drugs that can be useful in treating hypertension are desirable.

In view of current interest in the art for finding useful antihypertensive and useful antiviral agents, in particular, useful agents against herpes group viruses, any new compounds exhibiting antihypertensive activity or antiviral activity would be a welcome contribution to the art. This invention provides such a contribution.

SUMMARY OF THE INVENTION

This invention provides compounds which are useful as antiviral agents against DNA-containing viruses such as herpes group viruses. In particular, the compounds of this invention are useful against HSV-1 and HSV-2 and may also prove useful against CMV and EB.

The compounds of this invention are advantageous over known compounds because they inhibit early events in the viral replication. One embodiment of this invention provides antiviral compounds of Formula 1.0:

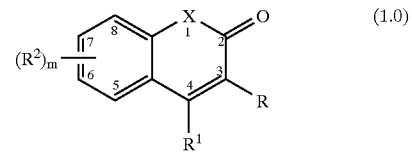

wherein
- (A) X is selected from the group consisting of N—$R^3$, O, S, and C($R^3$)$_2$;
- (B) $R^3$ is selected from the group consisting of:
  - (1) alkyl;
  - (2) aralkyl;
  - (3) aryl;
  - (4) substituted aryl;
  - (5) alkaryl;
  - (6) alkyl heteroaryl;
  - (7) aryloxyalkoxyalkyl;
  - (8) —(CH$_2$)$_j$R$^{20}$ wherein j is an integer from 1 to 6 and R$^{20}$ is selected from the group consisting of —C(O)OR$^{21}$, —OR$^{21}$, —R$^{21}$, and —N(R$^{21}$)$_2$, wherein each R$^{21}$ can be the same or different and is selected from the group consisting of alkyl, alkenyl and H; and
  - (9) —OR$^{22}$ wherein R$^{22}$ is selected from the group consisting of H, alkyl- which may be substituted with OH, SH, and/or NH$_2$—, alkaryl, alkenyl, and heteroaryl;
  - and the two groups $R^3$ on the same carbon atom can be the same or different;
- (C) R is selected from the group consisting of:
  - (1) —CH(OCOR$^4$)$_2$ wherein R$^4$ is selected from the group consisting of alkyl- which may be substituted with OH, SH, and/or NH$_2$—, aryl, alkaryl, alkenyl, and heteroaryl;
  - (2) —COR$^5$ wherein R$^5$ is selected from the group consisting of:
    - (a) H,
    - (b) alkyl- which may be substituted with OH, SH, and/or NH$_2$—,
    - (c) heteroaryl, (d) alkaryl,
(e) —NHR$^4$ wherein R$^4$ is as above defined,
(f) —N(R$^4$)$_2$ wherein R$^4$ is as above defined,
(g) alkenyl,
(h) substituted alkyl, and
(i) —NHO(O)R$^6$ wherein R$^6$ is selected from the group consisting of alkyl- which may be substituted with OH, SH, and/or NH$_2$—, aryl, alkaryl, heteroaryl, and H;
(3) —CO$_2$R$^6$ wherein R$^6$ is as defined above;
(4) —(CH$_2$)$_a$Y wherein a is an integer from 1 to 6 and Y is a halogen atom selected from the group consisting of Cl, F, Br and I;
(5) —(CH$_2$)$_b$R$^7$ wherein b is an integer of 1 to 6 and R$^7$ is a heteroaryl group;
(6) —S(O)$_c$—R$^8$ wherein c is 0 or an integer from 1 to 2 and R$^8$ is selected from the group consisting of alkyl- which may be substituted with OH, SH, and/or NH$_2$—, aryl, alkaryl, alkenyl, heteroaryl, heterocyclyl, and —(CH$_2$)$_d$OH wherein d is an integer from 1 to 6;
(7) heterocyclyl;
(8) —(CH$_2$)$_e$R$^9$ wherein e is an integer of 1 to 10, and R$^9$ is selected from the group consisting of aryl, alkenyl, —OR$^4$, —OH, —NO$_2$, —NHR$^4$, N(R$^4$)$_2$, —C(O)R$^5$, and —C(O)R$^6$, wherein each R$^4$ is the same or different, and wherein R$^4$, R$^5$, and R$^6$ are as above defined;
(9) aryl;
(10) —CH(OR$^6$)$_2$ wherein R$^6$ is as above defined;
(11) —CH=NOR$^{10}$ wherein R$^{10}$ is selected from the group consisting of H, alkyl, and —(CH$_2$)$_f$R$^{11}$ wherein f is an integer from 1 to 2 and R$^{11}$ is selected from the group consisting of —C(O)OH, phenyl, heteroaryl, —NHR$^4$, —N(R$^4$)$_2$, —SO$_3$H, and —SO$_2$NH$_2$, wherein R$^4$ is as above defined;
(12) —CH=N(CH$_2$)$_g$R$^{12}$ wherein g is an integer from 1 to 10, and R$^{12}$ is selected from the group consisting of —OH, —NHR$^4$, —N(R$^4$)$_2$, —C(O)OR$^6$, aryl, and heteroaryl, wherein R$^4$ and R$^6$ are as above defined;

(D) R$^1$ is selected from the group consisting of:
(1) —OR$^{14}$ wherein R$^{14}$ is selected from the group consisting of:
(a) alkyl;
(b) haloalkenyl having from 1 to 2 double bonds wherein the halogen atoms are selected from the group consisting of F, Cl, Br, and I;
(c) —(CH$_2$)$_h$—N(R$^{15}$)$_2$ wherein h is an integer from 1 to 6, and R$^{15}$ is selected from the group consisting of H and alkyl;
(d) acyl having the formula —C(O)R$^5$ wherein R$^5$ is as above defined; and
(e) —(CH$_2$)$_a$C(H)$_{3-i}$Z$_i$ wherein a is as above defined; Z is a halogen atom selected from the group consisting of Cl, F, Br and I; and i is an integer from 1 to 3, and when i is 2 or 3 each Z is the same or different;
(2) —NH$_2$;
(3) —NHR$^4$ wherein R$^4$ is as above defined;
(4) —N(R$^4$)$_2$ wherein R$^4$ is as above defined;
(5) —NHC(O)R$^6$ wherein R$^6$ is as above defined;
(6) —S(O)$_c$R$^4$ wherein c and R$^4$ are as above defined;
(7) —SR$^8$ wherein R$^8$ is as above defined;
(8) alkyl;
(9) aryl;
(10) alkaryl; and
(11) heteroaryl;

(E) m is 0 or an integer from 1 to 4;
(F) Each R$^2$ for each m is independently selected from the group consisting of:
(1) alkyl;
(2) alkoxy;
(3) aryloxy;
(4) aryl;
(5) aralkyloxy;
(6) halogen atoms selected from the group consisting of F, Cl, Br and I;
(7) —OCOR$^{4a}$ wherein R$^{4a}$ is selected from the group consisting of alkyl, substituted alkyl, aryl, substituted aryl, and heteroaryl;
(8) —N(R$^{16}$)$_2$ wherein each R$^{16}$ is independently selected from the group consisting of H, alkyl, aryl and R$^4$C(O)— wherein R$^4$ is as above defined;
(9) —CH$_2$OH;
(10) —COOH;
(11) —COOR$^{17}$ wherein R$^{17}$ is selected from the group consisting of alkyl and aryl;
(12) —SO$_3$H;
(13) —SO$_2$NR$^{18}$ wherein R$^{18}$ is selected from the group consisting of alkyl, aryl and H;
(14) —PO$_3$H;
(15) —OPO$_3$H; and
(16) —PO(OR$^{19}$)$_2$ wherein R$^{19}$ is selected from the group consisting of alkyl and aryl;
(17) —OPO(OR$^{19}$)$_2$ wherein R$^{19}$ is as above defined;

with the provisos that:
(1) when R is —CH(OC(O)R$^4$)$_2$ then R$^1$ is not —OR$^{14}$;
(2) when R is —C(O)R$^5$ then R$^1$ is not —OR$^{14}$; and
(3) when R is —CH(OR$^6$)$_2$ wherein R$^6$ is alkyl then R$^1$ is not —OR$^{14}$.

Another embodiment of this invention provides antihypertensive compounds represented by Formula 1.0 wherein:
(A) R$^2$, m, X and n are as above defined;
(B) R is a group —C(O)OR$^6$ wherein R$^6$ is as defined above; and
(C) R$^1$ is selected from the group consisting of:
(1) —OR$^{14}$ wherein R$^{14}$ is as above defined;
(2) —O(CH$_2$)$_h$N(R$^{15}$)$_2$ wherein h and R$^{15}$ are as defined above; and
(3) —O(CH$_2$)$_a$C(H)$_{3-i}$Z$_i$ wherein a, i and Z are as defined above;
and in particular from —OR$^{14}$ and —O(CH$_2$)$_h$N(R$^{15}$)$_2$ wherein h, R$^{14}$ and R$^{15}$ are as defined above.

Preferably, for the antihypertensive compounds, R$^6$ and R$^{15}$ are alkyl; most preferably R$^{15}$ is methyl and R$^6$ is ethyl. R$^{14}$ is preferably methyl. Preferably, h is 2, a is 1; or Z is Cl and i is 3. Preferably R is —C(O)OR$^6$ when R$^1$ is —O(CH$_2$)$_h$N(R$^{15}$)$_2$.

Another embodiment of this invention provides pharmaceutical compositions useful for treating viral infections or useful for treating antihypertension comprising an effective amount of an antiviral or an antihypertensive compound of this invention, together with a pharmaceutically acceptable carrier or excipient. Preferably the compounds having antiviral activity are selected from the group consisting of compounds represented by those numbered 1 to 33 in Table I below.

In yet another embodiment this invention provides a method of treating a patient suffering from hypertension or suffering from a viral infection by administering to such a patient an effective amount of an antihypertensive or antiviral compound of this invention. Generally, in the method of treatment, the compound is administered as one of the pharmaceutical compositions of this invention. Examples of viral infections treatable in accordance with the methods of this invention include the DNA-containing viruses such as the herpes viruses discussed above (e.g., HSV-1, HSV-2, CMV, VZ, EB, and the like).

DETAILED DESCRIPTION OF THE INVENTION

When used herein, the terms listed below have the scope indicated, unless indicated otherwise.

Alkaryl—represents an aryl group, as defined below, in which an alkyl group, as defined below, is substituted for one of the aryl H atoms. The aryl group may contain additional substituents selected from the group consisting of halogen atoms (e.g, Cl, Br, F, and/or I), alkoxy, alkyl, and amino. Representative examples include $CH_3$phenyl—, $CH_3CH_2$phenyl— and the like.

Alkenyl—represents straight and branched carbon chains having at least one carbon-to-carbon double bond and preferably having from 2 to 6 carbon atoms. Preferably the alkenyl substituent has from 1 to 2 double bonds. Representative examples include vinyl, allyl, butenyl and the like.

Alkoxy—represents an alkyl radical attached to a molecule through an oxygen atom (—O-alkyl). Representative examples include methoxy, ethoxy and the like.

Alkyl—represents straight or branched carbon chains, which contain from 1 to 6 carbon atoms. Representative examples include methyl, ethyl, propyl and the like.

Heteroarylalkyl—represents a heteroaryl group, as defined below, substituting an alkyl group, as defined above. Representative examples include pyridylmethyl, furylmethyl and the like.

Haloalkenyl—represents an alkenyl group, as defined above, wherein one or more hydrogen atoms are replaced by halogen atoms. The halogen atoms can be anywhere along the molecule, but alkenyl halides having the halogen atom at the terminal position of the halide are preferred. Preferably only one halogen atom is present in the halide substituent. The halogen atoms are selected from the group consisting of F, Cl, Br, and I. Preferably the halogen atom is selected from the group consisting of Cl and Br. Most preferably the halogen atom is Br. Representative examples include bromobutenyl, bromopropenyl and the like.

Aryloxyalkoxyalkyl—represents a group wherein an aryloxy group substitutes an alkoxy group which in turn substitutes another alkyl group wherein the oxygen atom is attached to the aryl group at a ring carbon atom. Alkoxy is as defined above and aryl is as defined below. The aryl group may contain additional substituents selected from the group consisting of halogen atoms (i.e., Cl, Br, F, and/or I), alkoxy, alkyl, and amino. Representative examples include phenoxypropoxymethyl, phenoxyethoxymethyl and the like.

Alkynyl—represents a straight or branched hydrocarbon chain having at least one carbon-to-carbon triple bond, and having from 3 to 8 carbon atoms with from 3 to 6 carbon atoms being preferred. Representative examples include propynyl, butynyl and the like.

Aralkyl—represents an alkyl group as defined above in which an aryl group as defined below is substituted for one of the alkyl hydrogen atoms. Representative examples include —$CH_2$phenyl, —$CH_2CH_2$phenyl, 4-hydroxybenzyl, 4-t-butyldimethylsilyloxybenzyl, and the like.

Aralkyloxy—represents an aralkyl group as defined above, which is attached to a molecule by an oxygen atom (aralkyl-O—). The aryl group may contain additional substitutents selected from the group consisting of halogen atoms (e.g., Cl, Br, F, and/or I), alkoxy, alkyl, and amino. Representative examples include benzyloxy, phenylethoxy, and the like.

Aryl—represents a mono or bi-cyclic aromatic system. Examples of preferred aryl groups include those having from 6 to 14 carbon atoms. Representative examples include phenyl, 1-naphthyl, 2-naphthyl and indanyl. The aryl group may contain additional substituents selected from the group consisting of halogen atoms (e.g., Cl, Br, F, and/or I), alkoxy, alkyl, and amino.

Aryloxy—represents an aryl group as defined above, which is attached through an oxygen atom (aryl-O—). The aryl may contain additional substituents selected from the group consisting of halogen atoms (e.g., Cl, Br, F, and/or I), alkoxy, alkyl, and amino. Representative examples include phenoxy, naphthyloxy,and the like.

Heteroaryl (including the heteroaryl portion of heteroarylmethyl)—represents aromatic systems having at least one O, S and/or N heteroatom in the ring structure. Examples of preferred heteroaryl groups include those containing from 3 to 14 carbon atoms. Representative examples of heteroaryl groups include but are not limited to: 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, 2-or 3-pyrrolyl, 2- or 3-N-methylpyrrolyl, and the like.

Heterocyclic (heterocyclyl)-represents non-aromatic cyclic groups having at least one O, S, and/or N heteroatom interrupting a carbocyclic ring structure containing from about 3 to about 6 carbon atoms. Preferably the heterocyclic groups contain about 3 to about 4 carbon atoms. Examples of heterocyclic groups include but are not limited to: thiazoline (thiazolinyl), thiazolidone (thiazolidinyl), dioxolane (dioxolanyl), morpholine (morpholinyl) and the like.

Substituted alkyl—represents an alkyl group, as defined above, wherein one or more of the alkyl H atoms are replaced with groups selected from the group consisting of alkyl, aryl, heteroaryl, —OH, —O-alkyl, —$NH_2$, —$N(alkyl)_2$ wherein each alkyl group is the same or different, —SH, —S-alkyl, —C(O)O-alkyl, —C(O)H, —NHC(:NH)$NH_2$, —C(O)$NH_2$, —OC(O)$NH_2$, —$NO_2$, —NHC(O)-alkyl, and —NHC(O)O-alkyl wherein alkyl, aryl, and heteroaryl are as above defined. Representative examples of substituted alkyl groups include hydroxyethyl, aminoethyl, mercaptoethyl, and the like.

Substituted aryl—represents an aryl group, as defined above, wherein one of more of the H atoms attached to the ring carbon atoms are replaced by groups independently selected from the group consisting of halo, alkyl, hydroxy, alkoxy, phenoxy, amino, alkylamino, and dialkylamino. Preferred substituted aryl groups are substituted phenyl groups.

As used herein, C(O) represents C=O.

In the compounds of this invention R is preferably selected from the group consisting of:

(1) —CH(OCOCH$_3$)$_2$;
(2) —CH(OCOC$_2$H$_5$)$_2$;
(3) —CH(OCOC$_4$H$_9$)$_2$;
(4) phenylmethyl;
(5) phenyl;
(6) —CH(OCH$_3$)$_2$;
(7) —CH$_2$OH;

(8) —CHO;
(9) —CO.OC$_2$H$_5$;
(10) —CH$_2$Br;

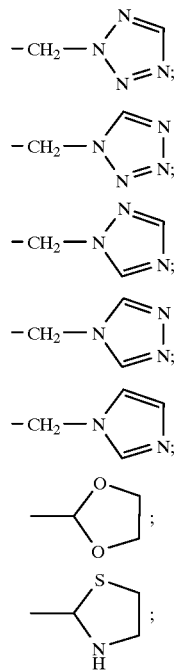

(18) —S—phenyl;
(19) —SCH$_3$;
(20) —CH=NOH;
(21) —SCH$_2$OH;
(22) —CH=NOCH$_3$;
(23) —CH=N(CH$_2$)$_2$OH;
and
(24) —S(O)CH$_3$.
and especially from those numbered 7 to 22 in this list.

R$^1$ is preferably OR$^{14}$ wherein R$^{14}$ is preferably selected from the group consisting of:
(1) —CH$_3$;
(2) —CH(CH$_3$)$_2$;
(3) —C$_2$H$_5$;
(4) —CH$_2$CH=CHCH$_2$Br;
(5) —NHCH$_2$CH$_2$OH;
(6) —CH$_2$CF$_3$;
(7) —CH$_2$CH$_2$N(CH$_3$)$_2$; and
(8) —COCH$_3$;

and especially from those numbered 1 and 7 in this list.

Preferably R$^2$ is selected from the group consisting of:
(1) —CH$_3$;
(2) —OCH$_3$;
(3) —OCOCH$_3$;
(4) phenylmethoxy;
(5) Cl;
(6) F;
(7) I; and
(8) —CF$_3$;

and especially from those numbered 1, 3 and 5 in this list.

Preferably R$^3$ is selected from the group consisting of:
(1) —CH$_3$;
(2) —C$_6$H$_{13}$;
(3) —C$_7$H$_{15}$;
(4) phenylmethyl;

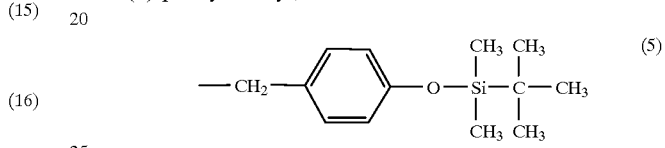

([(1,1-dimethylethyl)dimethylsiloxy]-phenylmethyl);

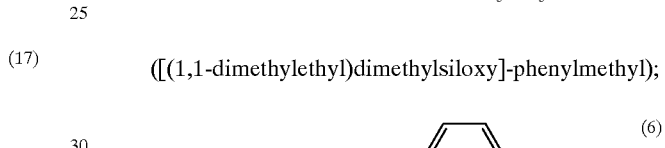

(3-(2-chloro-4-methoxyphenoxy)propoxymethyl);
(7) phenyl;
(8) —CH$_2$COOCH$_2$CH=CH$_2$;
and
(9) —CH$_2$COOCH$_3$;

and especially from those numbered 1 to 5 in this list.

Also, in the compounds of this invention X is preferably O or especially —NR$^3$, wherein R$^3$ is as defined above.

Further preferred compounds of Formula 1.0 include those wherein the radicals R, R$^1$ (as OR$^{14}$), R$^2$, and R$^3$ have the combined meanings given above.

Compounds of this invention include compounds of Formula 1.0 wherein X is NR$^3$ and which are selected from the group consisting of compounds represented by compounds numbered 1 to 33 set forth in Table I; characterizing data for such compounds are included later in the Examples:

TABLE I

| No. | R$^3$ | R | R$^1$ | R$^2$ |
|---|---|---|---|---|
| 1 | SiOBzl | —SCH$_3$ | —OCH$_3$ | 6-CH$_3$ 7-CH$_3$ |
| 2 | —C$_6$H$_{13}$ | 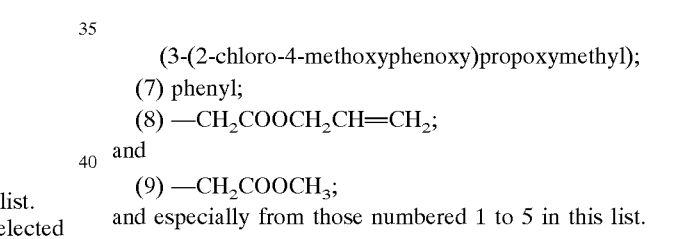 | —OCH$_3$ | — |

TABLE I-continued

| No. | R³ | R | R¹ | R² |
|---|---|---|---|---|
| 3 | —C₆H₁₃ | —CH=NOCH₃ | —OCH₃ | — |
| 4 | —C₆H₁₃ | —CH=NOH | —OCH₃ | 6-CH₃ |
| 5 | SiOBzl | —SCH₂OH | —O(CH₂)₂N(CH₃)₂ | 6-CH₃, 7-CH₃ |
| 6 | —C₆H₁₃ | 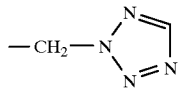 | —OCH₃ | — |
| 7 | Bzl | —C(O)OC₂H₅ | —OCH₃ | 6-CH₃ |
| 8 | —C₆H₁₃ | 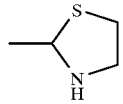 | —OCH₃ | 6-CH₃ |
| 9 | —C₆H₁₃ | —CH₂OH | —OCH₃ | 6-CH₃ |
| 10 | —C₆H₁₃ | 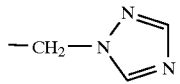 | —OCH₃ | 6-CH₃ |
| 11 | —C₆H₁₃ | 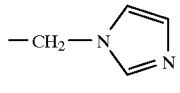 | —OCH₃ | 6-CH₃ |
| 12 | —C₆H₁₃ | 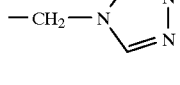 | —OCH₃ | 6-CH₃ |
| 13 | —C₆H₁₃ | 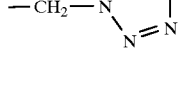 | —OCH₃ | 6-CH₃ |
| 14 | —C₆H₁₃ | 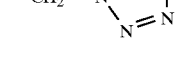 | —OCH₃ | 6-CH₃ |
| 15 | —C₆H₁₃ | —CH₂Br | —OCH₃ | — |
| 16 | —C₆H₁₃ | 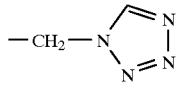 | —OCH₃ | — |
| 17 | —C₆H₁₃ | —CH=NOH | —OCH₃ | — |
| 18 | —C₆H₁₃ | 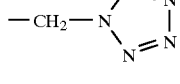 | —OCH₃ | — |
| 19 | —C₆H₁₃ | —C(O)OC₂H₅ | —OCH₃ | 6-CH₃ |
| 20 | Bzl | —CH=NOCH₃ | —OCH₃ | — |
| 21 | SiOBzl | —SCH₃ | —OCH₃ | 6-CH₃, 7-CH₃ |
| 22 | —CH₃ | phenylthio | —OCH₃ | 6-F |

TABLE I-continued

| No. | R³ | R | R¹ | R² |
|---|---|---|---|---|
| 23 | —C₆H₁₃ | 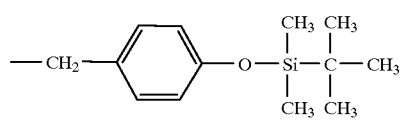 | —OCH₃ | 6-CH₃ |
| 24 | —C₆H₁₃ | 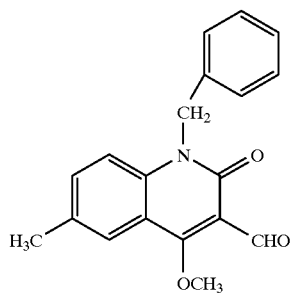 | —OCH₃ | — |
| 25 | 4-OHBzl | —SCH₃ | —OCH₃ | 6-CH₃ 7-CH₃ |
| 26 | —C₆H₁₃ | —CH=NOCH₃ | —OCH₃ | 6-CH₃ |
| 27 | Bzl | —C(O)OC₂H₅ | —O(CH₂)₂N(CH₃)₂ | 6-CH₃ |
| 28 | —C₆H₁₃ | —C(O)OC₂H₅ | —OCH₃ | 6-CH₃ |
| 29 | Bzl | —CH=NOH | —OCH₃ | — |
| 30 | Bzl | —CH=NOBzl | —OCH₃ | — |
| 31 | Bzl | —CH=NOCH₂CH=CH₂ | —OCH₃ | — |
| 32 | —C₆H₁₃ | —CH₂OH | —OCH₃ | — |
| 33 | —C₆H₁₃ | —CH₂Br | —OCH₃ | 6-CH₃ | wherein:

(1) SiOBzl represents

—CH₂—⟨C₆H₄⟩—O—Si(CH₃)₂—C(CH₃)₃

([(1,1-dimethylethyl)dimethylsiloxy]-phenylmethyl);

(2) Bzl represents phenylmethyl;

(3) Bzl-O represents phenylmethoxy; and (4) 4-OH Bzl represents 4-hydroxyphenylmethyl.

Compounds of this invention include compounds of Formula 1.0 wherein X is NR³ and which are selected from the following group numbered 1.20 to 1.22 and 1.26 to 1.28:

(1.20)

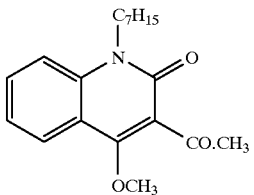

(1.21)

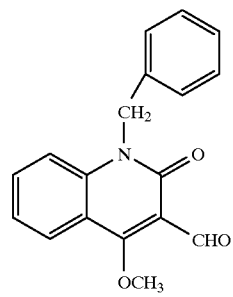

(1.22)

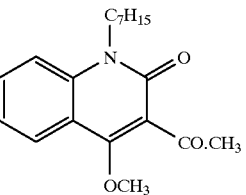

(1.26)

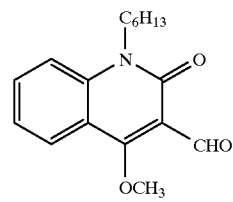

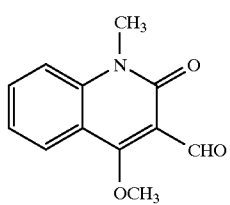

(1.27)

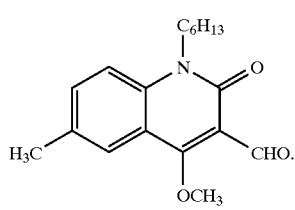

(1.28)

Compounds of this invention include compounds of Formula 1.0 wherein X is oxygen and which are selected from the following group numbered 65 to 71:

TABLE A

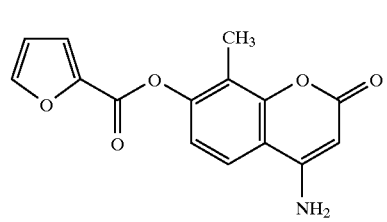

(65)

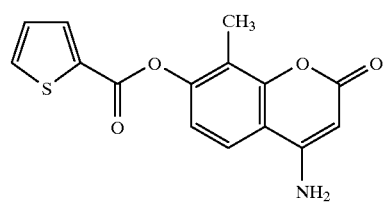

(66)

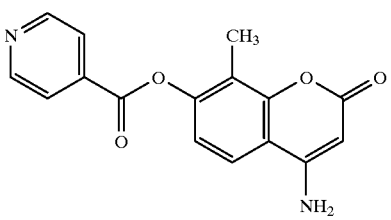

(67)

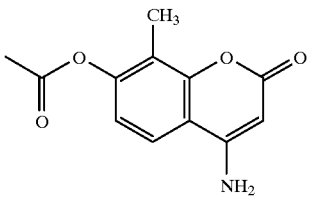

(68)

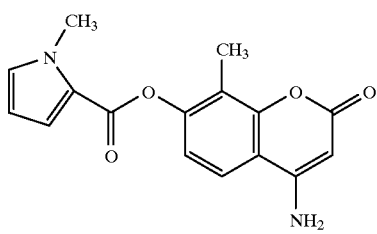

(69)

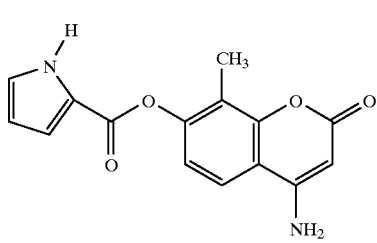

(70)

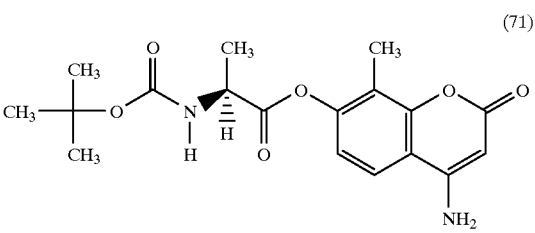

(71)

Of these, the compounds 70 and especially 69 are particularly preferred.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

Certain compounds of the invention will be acidic in nature, e.g., those compounds which possess a carboxyl or phenolic hydroxyl group. These compounds may form pharmaceutically acceptable salts. Examples of such salts are the sodium, potassium, calcium, and aluminum salts. Also contemplated are salts formed with pharmaceutically acceptable amines such as ammonia, alkylamines, hydroxyalkylamines, N-methylglucamine and the like.

Certain compounds of the invention, e.g., those with a basic amine group, also form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of this invention.

The compounds of Formula 1.0 can be prepared by standard processes such as those described below, and in particular the necessary intermediates and many of the products of Formula 1.0 can be obtained by the process steps outlined in Scheme I below. In these processes the substituents are as described above, unless indicated otherwise. Those skilled in the art will appreciate that in the processes described below the reactions are carried out at a temperature high enough to allow the reaction to proceed at a reasonable rate, but not so high as to cause undue degradation of reactants and/or products. Those skilled in the art will also appreciate that in the following reactions the desired products may be isolated by techniques well known in the art such as distillation, column chromatography, recrystallization, and the like.

In Scheme I, the various radicals and m are as defined for Formula 1.0; $X^1$ is $SR^8$, alkyl or aryl, $R^{23}$ is an esterifying group which may otherwise be the same as $R^6$ and is preferably a lower alkyl group, e.g., ethyl, and each $R^{24}$ is an inert organic group such as alkyl, especially a lower alkyl group such as ethyl or methyl, or the two groups $R^{24}$ together with the adjacent nitrogen atom can form a heterocyclic ring containing from 5 to 7 atoms and, if desired, a further heteroatom selected from O, S and N. All other radicals are as defined for Formula 1.0 above. Starting materials are indicated by underlining. Compounds of Formulae 2.3 and 2.8 are embraced by Formula 1.0 and are therefore compounds according to the invention, and are boxed; and routes from these to further products that are compounds of the invention of Formula 1.0 (also boxed) are indicated with an open arrow.

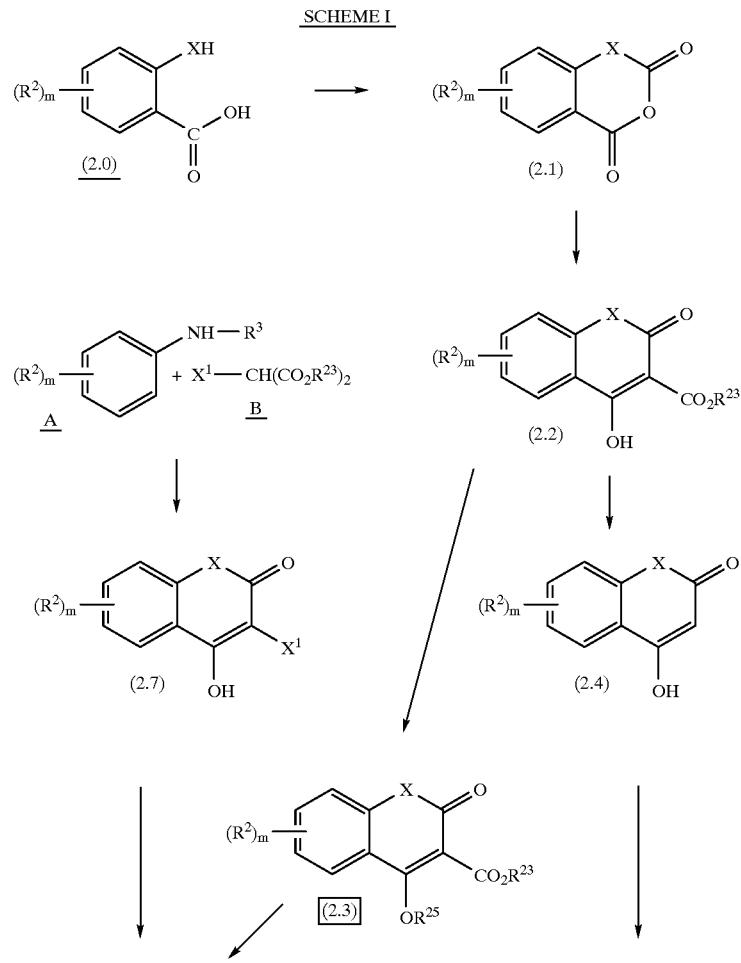

SCHEME I

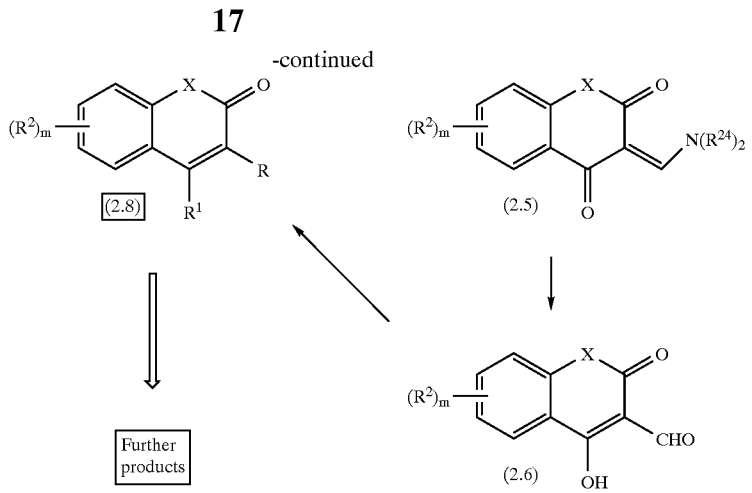

-continued

Further products

The conversion of a compound of Formula 2.0 into a compound of the Formula 2.1, and the conversion of a compound of the Formula 2.1 into a compound of the Formula 2.2, represent reactions well known to those skilled in the art; see for example G. M. Coppola et al., Synthesis, 505 (1980), the disclosure of which is incorporated herein by reference thereto.

In the first step, a suitable 2-substituted benzoic acid 2.0 in aqueous acid (e.g. 2N HCl) is reacted with trichloromethyl chloroformate to form a compound 2.1, which is an isatoic anhydride when X is NH or $NR^3$. The 2-substituted benzoic acid 2.0 will have the appropriate $R^2$ substituent group(s) to give the desired end product.

When X in the compound of Formula 1.0 is to be $NR^3$ (wherein $R^3$ must be other than hydrogen) but is NH in the isatoic anhydride of the Formula 2.1, then this compound of the Formula 2.1 can be reacted with a suitable $R^3$-halide (wherein $R^3$ is as above defined) to produce the desired $R^3$-substituted isatoic anhydride of the Formula 2.1. This is also disclosed by G. M. Coppola et al., Synthesis, 505 (1980).

In the second step, the compound of Formula 2.1 is reacted with the anion derived from a malonate ester to produce the compound of the Formula 2.2 (which is a quinolinone when X is $NR^3$). $R^{23}$ is ethyl when diethyl malonate is used in the malonate condensation.

The compound of the Formula 2.2 can be decarboxylated to produce the compound of the Formula 2.4 by procedures well known in the art, for example by reaction with alkali—see G. M. Coppola et al, J. Org. Chem., A41, 825 (1976), the disclosure of which is incorporated herein by reference thereto.

The compound of the Formula 2.4 can then be converted into the disubstituted aminomethylene dione (enamine) of the Formula 2.5 by reaction with an excess of a dimethylformamide dialkylacetal in an appropriate solvent for a few hours, e.g., with dimethylformamide dimethylacetal in a low boiling solvent such as dichloromethane.

The enamine of the Formula 2.5 can then be hydrolyzed to afford the aldehyde of the Formula 2.6.

A compound of the Formula 2.7 wherein $X^1$ is $—S—R^8$ (wherein $R^8$ is as defined above), alkyl or aryl, can be prepared by reaction of a substituted aniline of the Formula A

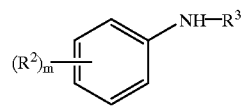

with a malonate ester of the Formula B $$X^1—CH(CO_2R^{23})_2 \qquad B$$

wherein $X^1$ and $R^{23}$ are as defined above, conveniently by heating equimolar quantities of the two reactants with or without a high boiling solvent, such as diphenylether, at temperatures within the range of about 150 to about 200° C. for a few hours.

The invention therefore provides a process for the preparation of compounds of Formula 1.0, which comprises one of the following steps (a) to (k):

(a) for the preparation of a compound of Formula 1.0 wherein R is $—COR^5$ wherein $R^5$ is a hydrogen atom, the reduction of a corresponding 3-esterified carboxy compound of the Formula 2.3:

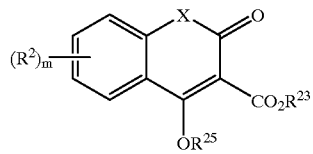

wherein X, $R^2$ and m are as defined for Formula 1.0, $R^{25}$ is an alkyl group having up to 6 carbon atoms, and $R^{23}$ is an alkyl group having up to 6 carbon atoms or a benzyl group, with an appropriate hydride reducing agent;

(b) for the preparation of a compound of Formula 1.0 wherein $R^1$ is an alkoxy group and R is $—COR^5$ wherein $R^5$ is an alkyl group, the reaction of a compound of the Formula 2.3 defined above, wherein $R^{25}$ and $R^{23}$ are as defined above, in solution in a suitable solvent, with a metal alkyl;

(c) for the preparation of a compound of the Formula 1.0 wherein R is $CH_2OH$, reduction of an aldehyde of the Formula 2.8

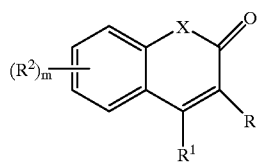

(2.8)

wherein R is CHO;

(d) for the preparation of a compound of the Formula 1.0 wherein R is —CH(OCOR⁴)₂, —CH(OR⁶)₂, —CH=NOR¹⁰, or —CH=N(CH₂)$_g$R¹², wherein R⁴, R⁶, R¹⁰, g and R¹² are as defined above, condensation of an aldehyde of the Formula 2.8 defined above wherein R is CHO with a compound of the formula HOCOR⁴, HOR⁶, H₂NOR¹⁰ or H₂N(CH₂)$_g$R¹², wherein R⁴, R⁶, R¹⁰, g and R¹² are as defined above;

(e) for the preparation of a compound of the Formula 1.0 wherein R is a group of the formula:

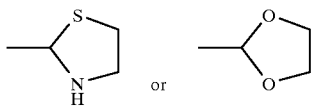

condensation of a compound of the Formula 2.8 defined above wherein R is an aldehyde group with ethane-1,2-diol or with 1-amino-ethane-2-thiol;

(f) for the preparation of a compound of the Formula 1.0 wherein R is —S(O)$_c$R⁴, the oxidation of a compound of Formula 2.8 defined above wherein R is —SR⁴;

(g) for the preparation of a compound of Formula 1.0 wherein R is CH₂Halogen, the halogenation of a compound of the Formula 1.0 wherein R is CH₂OH;

(h) for the preparation of a compound of the Formula 1.0 wherein R is a group of the formula:

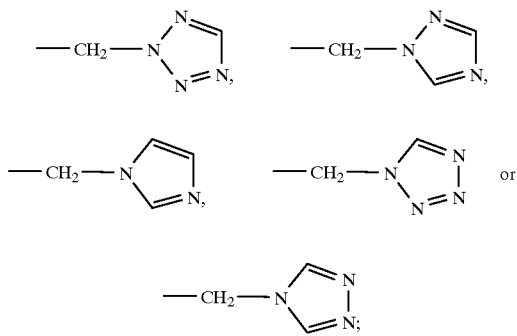

condensation of a compound of the Formula 1.0 wherein R is a halomethyl group with a heterocycle H-Het where Het has the formula:

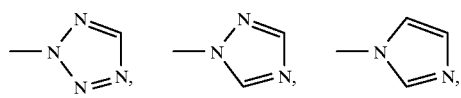

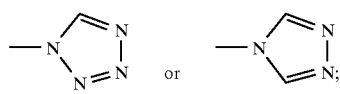

(i) for the preparation of a compound of Formula 2.3 wherein R²⁵ is alkyl, the reaction of a compound of Formula 2.2, or an ether-forming derivative thereof, with an alcohol R²⁵OH or with an ether-forming derivative thereof;

(j) for the preparation of a compound of Formula 1.0 wherein R¹ is OR¹⁴, wherein R¹⁴ is alkyl or a group of the formula —(CH₂)$_a$C(H)$_{3-i}$Z$_i$ wherein a, i and Z are as defined above for Formula 1.0, the reaction of a compound of Formula 2.8

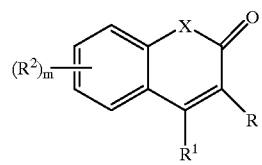

(2.8)

wherein R¹ of Formula 2.8 is lower alkoxy, by nucleophilic substitution with R¹⁴O⁻ (wherein R¹⁴ is not the same as R¹ but is otherwise as above defined) in solution in a solvent comprising an excess of the alcohol R¹⁴OH;

(k) for the preparation of a compound of Formula 1.0 wherein at least one group R² is —OCOR⁴a wherein R⁴a is as defined above, the esterification of a corresponding compound in which at least one group R² is a hydroxy group.

General reactions outlined above are disclosed more fully in (for example) J. March, *Advanced Organic Chemistry*, John Wiley and Sons, publishers, 1985, the disclosure of which is incorporated herein by reference thereto.

The compounds of this invention can be administered in any number of conventional dosage forms, e.g., topical, oral, parenteral, rectal, transdermal, inhalation and the like. Oral or rectal dosage forms include capsules, tablets, pills, powders, cachets, and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended for conversion, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration by employing an effective antiviral amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small amounts until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antiviral activity. For example, when administered orally doses of from about 20 to about 60 mg/kg of body weight may be used; and when administered parenterally, e.g., intravenously, dosages of from about 5 to about 20 mg/kg body weight may be used.

When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered rectally, the compounds of this invention may be administered in daily doses rangling from about 0.1 mg/kg to abut 100 mg/kg of body weight.

The dosage to be administered and the route of administration depends upon the particular compound used, the age and general health of the patient and the severity of the viral condition. Thus, the dose ultimately decided upon must be left to the judgment of a trained health-care practitioner.

EXAMPLES

The following Examples are illustrative only and should not be construed as limiting the invention in any way. Those skilled in the art will appreciate that variations are possible which are within the spirit and scope of the appended claims.

In the spectral data "Ar" is an abbreviation for aromatic, and Ph means phenyl.

PREPARATION A

Preparation of 1-Benzyl-4-Hydroxy-6-Methyl-2 (1H)-Quinolinone

Step (1): Preparation of 6-Methyl-Isatoic Anhydride.

A solution of 2-amino-5-methyl-benzoic acid (4.5 gm) in 2N HCl (15 ml) and water (35 ml) was stirred vigorously while adding dropwise trichloromethyl chloroformate (5.6 gm). The reaction was stirred for an additional 10 mins and then filtered; the solid cake was washed with water and dried under reduced pressure to give 6-methyl-isatoic anhydride as a light yellow powder (4.7 gm).

Step (2): Preparation of 1-Benzyl-6-Methyl-Isatoic Anhydride.

A solution of 6-methyl-isatoic anhydride (4.5 gm) in DMF (30 ml) was added dropwise to a stirred suspension of 60% sodium hydride (1.0 gm) in DMF (20 ml) under nitrogen atmosphere. The reaction was then warmed to 45° C. and stirred until hydrogen evolution ceased. It was then cooled and a solution of benzyl bromide (4.4 gm) in DMF (10 ml) was added slowly. Stirring was continued for one hour at room temperature and the solution was then evaporated under reduced pressure at 45° C. The resulting solid was suspended in methylene chloride, the insoluble inorganic solid was removed by filtration and the filtrate was evaporated to give 1-benzyl-6-methyl-isatoic anhydride as a crystalline solid.

Step (3): Preparation of 1-Benzyl-3-Ethoxycarbonyl-4-Hydroxy-6-Methyl-2(1H)-Quinolinone A solution of diethyl malonate (4.07 gm) in dimethyl acetamide (DMA) (10 ml) was added dropwise to a stirred suspension of 60% sodium hydride (1.01 gm) in the same solvent (10 ml), under a nitrogen atmosphere, in an oil bath at 25° C. After hydrogen evolution ceased, the temperature was raised to 80° C. while adding a solution of 1-benzyl-6-methyl-isatoic anhydride (4.5 gm) in DMA (50 ml). After carbon dioxide evolution ceased, the reaction mixture was heated at 120° C. for 17 hours and then was concentrated under reduced pressure to a volume of 25 ml. and then was diluted with water (50 ml). The milky solution was washed with ether, the aqueous layer was acidified with mineral acid to pH3 and the resulting crystalline product 1-benzyl-3-ethoxycarbonyl-6-methyl-2(1H)-quinolinone was isolated by filtration.

Step (4): Preparation of 1-Benzyl-4-Hydroxy-6-Methyl-2 (1H)-Quinolinone

The product from Step (3) was dissolved in 2N sodium hydroxide (150 ml) and the solution was refluxed for 4 hours. Then the solution was cooled and acidified with mineral acid to pH3. The solid was filtered, dried and crystallized from ethyl acetate/hexane to give 1-benzyl-4-hydroxy-6-methyl-2(1H)-quinolinone (4.0 gm). That the expected product was obtained was confirmed by the spectral data: MS: m/e 265 (M.$^+$); NMR (DMSO): δ2.32 (s, 3H, CH$_3$—Ar), 5.43 (s, 2H, CH$_2$—Ar), 5.96 (s, 1H, =CH—), 11.48 (s, 1H, OH) ppm.

PREPARATION B

Preparation of 1-Methyl-3-Formyl-4-Hydroxy-2 (1H)-Quinolinone

Step (1): Preparation of 1-methyl-3-dimethyl-aminomethylene-(1H)-quinolin-2,4-dione A suspension of 1-methyl-4-hydroxy-2(1H)-quinolinone (1.0 gm) in dimethyl formamide dimethyl acetal (5 ml) and methylene chloride (2.0) was refluxed for 1 hour. The resulting dark orange solution was evaporated under reduced pressure to give 1-methyl-3-dimethylaminomethylene-(1H)-quinolin-2,4-dione.

Step (2): Preparation of 1-methyl-3-formyl-4-hydroxy-2 (1H)-quinolinone.

The product from Step (1) was dissolved in distilled water (50 ml) by gentle warming and then the resulting solution was filtered. The clear filtrate was cooled in an ice bath and acidified to pH3 with mineral acid. The resulting crystalline precipitate was washed with water and dried to give 1-methyl-3-formyl-4-hydroxy-2(1H)-quinolinone. That the expected product was obtained was confirmed by the spectral data: MS: m/e 203 (M.$^+$); NMR (CDCl$_3$): δ3.6 (s, 3H, NCH$_3$), 10.28 (s, 1H, CHO) ppm.

PREPARATION C 1-(4-t-Butydimethylsilyloxybenzyl)-3-Methylthio-4-Hydroxy-6,7-Dimethyl-2(1H)-Quinolinone Step (1): Preparation of N-(4-t-Butyldimethylsilyloxy-benzyl)-3,4-dimethylaniline A mixture of 3,4-dimethylaniline (30 g) and p-hydroxybenzaldehyde (30 g) in benzene (500 ml) and dimethylformamide (170 ml) was refluxed for 4 hours with removal of water using a Dean Stark trap. The reaction was then evaporated to dryness under reduced pressure, the crude residue was dissolved in ethanol (300 ml), and then the resulting solution was treated with sodium borohydride (8.98 g) and heated at 50° C. for 3 hours. The reaction was then concentrated under reduced pressure, then diluted with water and then extracted with methylene chloride. The organic extract was dried over sodium sulfate, evaporated to dryness and the residue was dissolved in dimethylformamide (400 ml) containing imidazole (14.15 g). To this solution was added t-butyldimethylsilylchloride (30 g) in dimethylformamide (100 ml). The mixture was stirred for 24 hours, and then evaporated under reduced pressure. The residue was then extracted with hexane. The hexane extracts upon evaporation and chromatography on silica gel gave the title compound. That the expected product was obtained was confirmed by the spectral data: MS(CI): m/e 342 (M$^+$.+1); NMR (CDCl$_3$): δ0.19 (s, 6H, CH$_3$—Si); 0.98 (s, 9H, t-butyl), 2.15 (s, 3H, CH$_3$—Ar), 2.19 (s, 3H, CH$_3$—Ar), 4.21 (s, 2H, CH$_2$—Ar).

Step (2): Preparation of 1-(4-t-Butyldimethylsilyloxy-benzyl)-3-methylthio-4-hydroxy-6,7-dimethyl-2-(1H)-Quinolinone.

A mixture of the product from Step (1) (10 g) and 2-methylthio-malonic acid diethyl ester (6 g) was heated in an oil bath at 220° C. for 90 minutes. The reaction was then cooled to room temperature, dissolved in methylene chloride and the title compound was allowed to crystallize out from the solution. That the expected product was obtained was confirmed by the spectral data: MS (CI): m/e 456 (M$^+$.+1); NMR (CDCl$_3$): δ0.15 (s, 6H, CH$_3$—Si), 0.95 (s, 9H, t-butyl), 2.28, 2.30 (s, 6H, (CH$_3$)$_2$Ar), 2.39 (s, 3H, CH$_3$—S), 5.45 (s, 2H, CH$_2$Ar), 7.75 (s, 1H, C$_5$—H).

EXAMPLES 1 TO 34

Example 1

1-Hexyl-3-[2-(1,3-dioxolano)]-4-methoxy-6-methyl-2(1H)-Quinolinone (Compound No. 23 of Table I)

Step (1): Following the procedure set forth in Steps (2) and (3) of Preparation A, hexyl bromide was utilized instead of benzyl bromide to produce 1-hexyl-3-ethoxycarbonyl-4-hydroxy-6-methyl-2(1H)-quinolinone Step (2): Then a solution of the 1-hexyl-3-ethoxycarbonyl-4-hydroxy-6-methyl-2(1H)-quinolinone (12.4 g) in dichloromethane (50 ml) and methanol (10 ml)

was treated with excess diazomethane in ether for 10 mins. This solution was then evaporated. The crude methylation product upon chromatography on silica gel yielded 1-hexyl-3-ethoxycarbonyl-4-methoxy-6-methyl-2(1H)-quinolinone (11.5 g). The 1-hexyl-3-ethoxycarbonyl-4-methoxy-6-methyl-2(1H)-quinolinone (7.13 g) in dry toluene (80 ml) was cooled to −78° C. and then a 1M solution of di-isobutyl aluminum hydride (30 ml) was added dropwise in 10 min. After 2.5 hours of stirring at −78° C. the reaction mixture was worked up by stirring with aqueous ammonium chloride/1N hydrochloric acid which was then followed by extraction with methylene chloride. The crude reduction product was chromatographed on silica gel and then crystallized from ethyl acetate/hexane to give 1-hexyl-3-formyl-4-methoxy-6-methyl-2(1H)-quinolinone. That the expected product was obtained was confirmed by the spectral data: MS(CI): m/e 302 (M$^+$.1); NMR (CDCl$_3$): δ2.42 (s, 3H, Ar—CH$_3$), 4.10 (s, 3H, OCH$_3$), 10.50 (s, 1H, CHO).

Step (3): Then a solution of 1-hexyl-3-formyl-4-methoxy-6-methyl-2(1H)-quinolinone (1 g) in benzene (20 ml), containing ethylene glycol (2 ml) and p-toluenesulfonic acid (0.2 9) was refluxed for 3 hours with removal of water. The mixture was then cooled, washed with aqueous sodium bicarbonate, dried, evaporated and crystallized from ether to give 1-Hexyl-3-[2-(1,3-dioxolano)]-4-methoxy-6-methyl-2(1H)-quinolinone. That the expected product was obtained was confirmed by the spectral data: MS: m/e 345 (M.$^+$); NMR (CDCl$_3$): δ3.98 (s, 3H, OCH 3), 4.02, 4.32 (m, 4H, CH$_2$O), 6.38 (s, 1H, —OCHO—).

Example 2

1-Hexyl-3-(2-thiazolidinyl)-4-methoxy-6-methyl-2 (1H)-Quinolinone (Compound No. 8 of Table I)

A solution of 1-hexyl-3-formyl-4-methoxy-6-methyl-2 (1H)-quinolinone (Step (2) of Example 1, 1 g) and 2-aminoethanethiol (0.26 g) in methylene chloride (20 ml) containing p-toluenesulfonic acid (0.1 g) was stirred for 3 hrs. The mixture was washed with aqueous sodium bicarbonate, dried, evaporated and then crystallized from ether-hexane to give 1-Hexyl-3-(2-thiazolidinyl)-4-methoxy-6-methyl-2(1H)-quinolinone. That the expected product was obtained was confirmed by the spectral data: MS: m/e 360(M.$^+$); NMR (CDCl$_3$): δ3.17 (m, 2H, CH$_2$S), 3.86 (m, 2H, CH$_2$N), 6.0 (d, 1H, S—CH—N).

Example 3

1-Hexyl-3-(2-thiazolidinyl)-4-methoxy-2(1H)-Quinolinone (Compound No. 2 of Table I)

Step (1): Using the procedure set forth in Steps (1) to (3) of Preparation A, 1-hexyl-3-ethoxycarbonyl-4-hydroxy-2 (1H) quinolinone was produced using hexyl bromide and isatoic anhydride.

Step (2): Following the procedure set forth in Step (2) of Example 1, 1-hexyl-3-ethoxycarbonyl-4-hydroxy-2(1H) quinolinone was converted to 1-hexyl-3-formyl-4-methoxy-2(1H) quinolinone. That the expected product was obtained was confirmed by the spectral data: MS(FAB): m/e 288 (M$^+$.+1); NMR (CDCl$_3$): δ4.12 (s, 3H, OCH$_3$), 10.5 (s, 1H, CHO).

Step (3): Following the procedure set forth in Example 2, 1-hexyl-3-formyl-4-methoxy-2(1H) quinolinone was converted to 1-Hexyl-3-( 2-thiazolidinyl)-4-methoxy-2(1H)-quinolinone. That the expected product was obtained was confirmed by the spectral data: MS: m/e 346 (M.$^+$); NMR (CDCl$_3$): δ4.05 (s, 3H, OCH$_3$), 6.0 (s, 1H, S—CH—N).

Example 4

1-Hexyl-3-Oximinomethyl-4-Methoxy-6-Methyl-2 (1H )-Quinolinone (Compound No. 4 of Table I)

A solution of 1-hexyl-3-formyl-4-methoxy-6-methyl-2 (1H)-quinolinone (Step (2) of Example 1, 1 g), hydroxylamine hydrochloride (0.3 g) and sodium acetate (0.3 g) in methanol (20 ml) was stirred for 3hrs. The mixture was then diluted with water and extracted with methylene chloride. The extracts were dried, evaporated and the resulting solid was crystallized from ether-hexane to give 1-hexyl-3-oximinomethyl-4-methoxy-6-methyl-2(1H)-quinolinone. That the expected product was obtained was confirmed by the spectral data: MS: m/e 316 (M.$^+$); NMR (CDCl$_3$): δ3.98 (s, 3H, OCH$_3$), 8.54 (s, 1H, CH═N).

Example 5

1-Hexyl-3-Hydroximinomethyl-4-Methoxy-2(1H)-Quinolinone (Compound No. 4 of Table I)

Following the procedure set forth in Example 4, 1-hexyl-3-formyl-4-methoxy-2(1H) quinolinone (Step (2) of Example 3) was converted to 1-hexyl-3-hydroximinomethyl-4-methoxy-2(1H)-quinolinone. That the expected product was obtained was confirmed by the spectral data: MS: m/e 302 (M.$^+$); NMR (CDCl$_3$): δ4.0 (s, 3H, OCH$_3$), 8.58 (s, 1H, CH═N).

Example 6

1-Hexyl-3-Methoximinomethyl-4-Methoxy-6-Methyl-2(1H)-Quinolinone (Compound No. 26 of Table I)

Following the procedure set forth in Example 4, with the exception that methoxylamine hydrochloride was used instead of hydroxylamine hydrochloride, 1-hexyl-3-methoximinomethyl-4-methoxy-6-methyl-2(1H)-quinolinone was obtained. That the expected product was obtained was confirmed by the spectral data: MS: m/e 330 (M.$^+$); NMR (CDCl$_3$): δ4.0 (s, 3H, OCH$_3$), 4.05 (s, 3H, OCH$_3$, 8.45 (s, 1H, CH═N).

Example 7

1-Hexyl-3-Methoximinomethyl-4-Methoxy-2(1H)-Quinolinone (Compound No. 3 of Table I)

Following the procedure set forth in Example 5, with the exception that methoxylamine hydrochloride was used instead of hydroxylamine hydrochloride, 1-hexyl-3-methoximinomethyl-4-methoxy-2(1H)-quinolinone was obtained. That the expected product was obtained was confirmed by the spectral data: MS: m/e 316 (M.$^+$);

Example 8

1-Benzyl-3-Hydroximinomethyl-4-Methoxy-2(1H)-Quinolinone (Compound No. 29 of Table I)

Step (1): Following the procedure set forth in Preparation A, with the exception that isatoic anhydride was used instead of 6-methyl isatoic anhydride, 1-benzyl-3-ethoxycarbonyl-4-hydroxy-2(1H)-quinolinone was obtained.

Step (2): Following the Procedure set forth in Step (2) of Example 1 and using 1-benzyl-3-ethoxycarbonyl-4-hydroxy-2(1H)-quinolinone, 1-benzyl-3-formyl-4-methoxy-2(1H)-quinolinone was obtained. That the expected product was obtained was confirmed by the spectral data: MS: 293 (M.$^+$); NMR (CDCl$_3$): δ4.20 (s, 3H, OCH$_3$), 10.50 (s, 1H, CHO).

Step (3): Following the procedure described in Example 4, 1-benzyl-3-formyl-4-methoxy-2(1H)-quinolinone was converted to 1-benzyl-3-hydroximinomethyl-4-methoxy-2(1H)-quinolinone. That the expected product was obtained was confirmed by the spectral data: MS: m/e 308 (M.$^+$); NMR (DMSO): δ4.0 (s, 3H, OCH$_3$), 5.52 (s, 2H, CH$_3$—Ar), 8.26 (s, 1H, CH=N), 11.50 (s, 1H, NOH).

Example 9

1-Benzyl-3-Methoxyiminomethyl-4-Methoxy-2(1H)-Quinolinone (Compound No. 20 of Table I)

Following the procedure set forth in Example 8, with the exception that methoxyamine hydrochloride was used instead of hydroxylamine hydrochloride, 1-benzyl-3-methoxyiminomethyl-4-methoxy-2(1H)-quinolinone was obtained. That the expected product was obtained was confirmed by the spectral data: MS: m/e 322 (M.$^+$); NMR (CDCl$_3$): δ4.05 (s, 3H, OCH$_3$), 4.55 (s, 2H, CH$_3$Ar), 8.51 (s, 1H, CH=N).

Example 10

1-Benzyl-3-Benzyloxyiminomethyl-4-Methoxy-2(1H)-Quinolinone (Compound No. 30 of Table I)

Following the procedure set forth in Example 8 with the exception that benzyloxyamine hydrochloride was used instead of hydroxylamine hydrochloride, 1-benzyl-3-benzyloxyiminomethyl-4-methoxy-2(1H)-quinolinone was obtained. That the expected product was obtained was confirmed by the spectral data: MS: m/e 398 (M$^+$.); NMR (CDCl$_3$): δ3.85 (s, 3H, CH$_3$), 5.28 (s, 2H, OCH$_2$Ph), 5.52 (s, 2H, OCH$_2$Ph), 8.60 (s, 1H, CH=N).

Example 1

1-Benzyl-3-Allyloxyiminomethyl-4-Methoxy-2(1H)-Quinolinone (Compound No. 31 of Table I)

Following the procedure set forth in Example 8, with the exception that allyloxyamine hydrochloride was used instead of hydroxylamine hydrochloride, 1-benzyl-3-allyloxyiminomethyl-4-methoxy-2(1H)-quinolinone was obtained. That the expected product was obtained was confirmed by the spectral data: MS: m/e 348 (M.$^+$); NMR (CDCl$_3$): δ4.02 (s, 3H, OCH$_3$), 5.30 (m, 2H, CH$_2$=), 5.55 (s, 2H, CH$_2$Ph), 6.10 (m, 1H, CH=) 8.58 (s, 1H, CH=N).

Example 12

1-Hexyl-3-Hydroxymethyl-4-Methoxy-6-Methyl-2(1H)-Quinolinone (Compound No. 9 of Table I)

A solution of 1-hexyl-3-formyl-4-methoxy-6-methyl-2(1H)-quinolinone (Step (2) of Example 1, 10 g) in methanol (80 ml) was cooled in an ice-bath and stirred while adding, in small lots, solid sodium borohydride (0.5 g). After stirring for an additional 5 mins the reaction mixture was carefully diluted with water and extracted with methylene chloride. The extracts are dried and evaporated under reduced pressure. The crude product is chromatographed on silica-gel. Elution with 30% acetone-hexane gave 1-hexyl-3-hydroxymethyl-4-methoxy-6-methyl-2(1H)-quinolinone. That the expected product was obtained was confirmed by the spectral data: MS: m/e 303 (M.$^+$); NMR (CDCl$_3$): δ4.0 (s, H, OCH$_3$), 4.75 (d, 2H, CH$_2$O).

Example 13

1-Hexyl-3-Hydroxymethyl-4-Methoxy-2(1H)-Quinolinone (Compound No. 32 of Table I)

Following the procedure set forth in Example 12, 1-hexyl-3-formyl-4-methoxy-2(1H)-quinolinone (Step (2) of Example 3) was converted to 1-hexyl-3-hydroxymethyl-4-methoxy-2(1H)-quinolinone. That the expected product was obtained was confirmed by the spectral data: MS: m/e 289 (M.$^+$).

Example 14

1-Hexyl-3-Bromomethyl-4-Methoxy-6-Methyl-2(1H)-Quinolinone (Compound No. 33 of Table I)

A solution of 1-hexyl-3-hydroxymethyl-4-methoxy-6-methyl-2(1H)-quinolinone (Example 12, 0.6 g) in methylene chloride (12 ml) containing carbon tetrabromide (1 g) was treated with triphenylphosphine (0.87 g) and stirred at ice bath temperature for 5 mins and then at room temperature for 1 hr. The reaction mixture was then evaporated under reduced pressure and the crude product was chromatographed on silica-gel (25 g). Elution with 50% ether-hexane gave 1-hexyl-3-bromomethyl-4-methoxy-6-methyl-2(1H)-quinolinone as a white crystralline solid. That the expected product was obtained was confirmed by the spectral data: MS: m/e 365,367 (M.$^+$); NMR (CDCl$_3$): δ4.12 (s, 3H, OC$_3$) 4.68 (s, 2H, CH$_2$Br).

Example 15

1-Hexyl-3-Bromomethyl-4-Methoxy-2(1H)-Quinolinone (Compound No. 15 of Table I)

Following the procedure described in Example 14, 1-hexyl-3-hydroxymethyl-4-methoxy-2(1H)-quinolinone (Example 13) was converted to 1-hexyl-3-bromomethyl-4-methoxy-2(1H)-quinolinone. That the expected product was obtained was confirmed by the spectral data: MS: m/e 351, 353 (M.$^+$); NMR (CDCl$_3$); δ4.10 (s, 3H, OCH$_3$), 4.68 (s, 2H, CH$_2$Br).

Example 16

1-Hexyl-3-(1H-imidazol-1-ylmethyl)-4-methoxy-6-methyl-2(1H)-quinolinone (Compound No. 11 of Table I)

A solution of imidazole (0.07 g) in dimethylformamide (1.5 ml) was stirred with 60% sodium hydride (0.04 g) at ice-bath temperature under nitrogen until the reaction was complete. The reaction mixture was then treated with a solution of 1-hexyl-3-bromomethyl-4-methoxy-6-methyl-2(1H)-quinolinone (Example 14, 0.27 g) in dimethylformamide (3 ml) and stirred at room temperature for 2 hours. The solution was then diluted with ethyl acetate and washed several times with water. The organic layer was then dried and evaporated under reduced pressure. The crude reaction product was chromatographed on silica-gel (44 g). Elution with 2% methanoldichloromethane gave 1-hexyl-3-(1H-imidazol-1-ylmethyl)-4-methoxy-6-methyl-2(1H)-quinolinone which crystallized as a white solid. That the expected product was obtained was confirmed by the spectral data: MS: m/e 353 (M.$^+$); NMR (CDCl$_3$): δ3.90 (s, 3H, OCH$_3$), 5,18 (s, 2H, CH$_2$-Im), 6.99, 7.14, 7.72 (s, 3H, CH=) wherein Im represents imidazole.

Example 17

1-Hexyl-3-(1,2,4-Triazol-1-ylmethyl)-4-Methoxy-6-Methyl-2(1H)-Quinolinone (Compound No. 10 of Table I)

A solution of 1,2,4-triazole (0.033 g) in dimethylformamide (0.7 ml) was stirred at ice-bath temperature with 60% sodium hydride (0.02 g) for 10 mins under nitrogen and then a solution of 1-hexyl-3-bromomethyl-4-methoxy-6-methyl-2(1H)-quinolinone (Example 14, 0.14 g) in dimethylformamide (1.7 ml) was added to it. The mixture was stirred at room temperature for 2 hours, then diluted with ethyl acetate and then washed several times with water. The organic layer was dried and evaporated under reduced pressure. The resulting crude reaction product was chromatographed on silica-gel (4 g). Elution with 2.5% methanol-ethyl acetate gave 1-hexyl-3-(1,2,4-triazol-1-ylmethyl)-4-methoxy-6-methyl-2(1H)-quinolinone as white crystals (80%). That the expected product was obtained was confirmed by the spectral data: MS: m/e 354 (M.$^+$); NMR (CDCl$_3$): δ4.15 (s, H, OCH$_3$), 5.42 (s, 2H, CH$_2$), 7.86, 8.5 (s, 2H, CH=).

Further elution with 5% methanol-acetate gave the isomeric 1-hexyl-3-(1,2,4-triazol-4-ylmethyl)-4-methoxy-6-methyl-2(1H)-quinolinone as the minor product. That this compound was obtained was confirmed by the spectral data: MS: m/e 354 (M.$^+$); NMR (CDCl$_3$): δ4.0 (s, 3H, OCH$_3$), 5.22 (s, 2H, CH$_2$), 8.40 (s, 2H, CH=).

Example 18

1-Hexyl-3(1,2,4-Triazol-1-ylmethyl)-4-Methoxy-2 (1H)-Quinolinone (Compound No. 16 of Table I)

Following the procedure set forth in Example 17, 1-hexyl-3-bromomethyl-4-methoxy-2(1H)-quinolinone (Example 15) was converted to 1-hexyl-3(1,2,4-triazol-1-ylmethyl)-4-methoxy-2(1H)-quinolinone. That the expected product was obtained was confirmed by the spectral data: MS: m/e 340 (M.$^+$); NMR (CDCl$_3$): δ4.15 (s, 3H, OCH3), 5.46 (s, 2H, CH$_2$), 7.92 (s, 1H, CH=), 8.61 (s, 1H, CH=). The 1-hexyl-3(1,2,4-triazol-1-ylmethyl)-4-methoxy-2(1H)-quinolinone was obtained in 80% yield along with the isomeric 1-hexyl-3-(1,2,4-triazol-4-ylmethyl)-4-methoxy-2(1H)-quinolinone. That the expected product was obtained was confirmed by the spectral data: [MS: m/e 340 (M.$^+$); NMR (CDCl$_3$): δ4.0 (s, 3H, OCH$_3$), 5.21 (s, 2H, CH$_2$), 8.40 (s, 2H, CH=), 8.61 (s, 1H, CH=).

Example 19

1-Hexyl-3-(1-Tetrazolylmethyl)-4-Methoxy-6-Methyl-2(1H)-Quinolinone (Compound No. 14 of Table I)

A solution of tetrazole (0.17 g) in dimethylformamide (2 ml) at ice-bath temperature under nitrogen was stirred with 60% sodium hydride (0.1 g) for 5 mins and then a solution of 1-hexyl-3-bromomethyl-4-methoxy-6-methyl-2(1H)-quinolinone (Example 14, 0.73 g) in dimethylformamide (8 ml) was added to it. The reaction mixture was stirred at room temperature for 2 hours, diluted with ethylacetate and then washed several times with water. The organic layer was dried and evaporated under reduced pressure. The resulting crude reaction product was chromatographed on silica-gel (30 g). Elution with 10% to 20% ethylacetatedichloromethane gave 1-hexyl-3-(1-tetrazolylmethyl)-4-methoxy-6-methyl-2(1H)-quinolinone (0.37 g). That this compound was obtained was confirmed by the spectral data: MS: m/e 355 (M.$^+$); NMR (CDCl$_3$): δ4.18 (s, 3H, OCH$_3$), 5.68 (s, 2H, CH$_2$), 9.14 (s, 1H, CH=).

The isomeric 1-hexyl-3-(2-tetrazolylmethyl)-4-methoxy-6-methyl-2(1H)-quinolinone (Compound No. 13 of Table I) (0.28 g) was also obtained. That this compound was obtained was confirmed by the spectral data: MS: m/e 355 (M.$^+$); NMR: (CDCl$_3$): δ4.0 (s, 3H, OCH$_3$), 5.90 (s, 2H, CH$_2$), 8.48 (s, 1H, CH=).

Example 20

1-Hexyl-3-(1-tetrazolymethyl)-4-methoxy-2(1H)-quinolinone (Compound No. 18 of Table I)

Following the procedure set forth in Example 19, 1-hexyl-3-bromomethyl-4-methoxy-2(1H)-quinolinone was converted to 1-hexyl-3-(1-tetrazolymethyl)-4-methoxy-2(1H)-quinolinone. That this compound was obtained was confirmed by the spectral data: MS: m/e 341 (M.$^+$); NMR (CDCl3): δ4.0 (s, 3H, OCH$_3$), 5.91 (s, 2H, CH$_2$), 8.50 (s, 1H, CH=).

The isomeric 1-hexyl-3-(2-tetrazolylmethyl)-4-methoxy-2(1H)-quinolinone was also obtained. That this compound was obtained was confirmed by the spectral data: MS: m/e 341 (M.$^+$); NMR (CDCl$_3$): δ4.18 (s, 3H, OCH$_3$), 5.70 (s, 2H, CH$_2$), 9.12 (s, 1H, CH=).

Example 21

1-(4-t-Butyldimethylsilyloxybenzyl)-3-Methylthio-4-Methoxy-6,7-Dimethyl-2-(1H)-Quinolinone (Compound No. 21 of Table I)

A solution of the product from Preparation C (1.0 g) in dichloromethane (10 ml) and methanol (1.0 ml) was treated with an excess of ethereal diazomethane for 15 minutes and then evaporated with a stream of nitrogen. The residue was chromatographed on silica gel to give the title compound. That the expected product was obtained was confirmed by the spectral data: MS: m/e 469 (M.$^+$); NMR (CDCl$_3$): δ0.15 (s, 6H, CH$_3$Si), 0.95 (s, 9H, t-butyl), 2.28, 2.30 (s, 6H, CH$_3$—Ar), 2.57 (s, 3H, CH$_3$S), 3.80 (s, 3H, OCH$_3$), 5.46 (s, 2H, CH$_2$—Ar), 7.63 (s, 1H, C-5H).

Those skilled in the art will recognize that Compounds numbered 1, 5–7, 12–13, 17, 19, 22, 24–25, and 27–28 of Table I can be prepared in accordance with the procedures exemplified above.

Example 22

4-Amino-7-(N-Methyl-Pyrrol-2-Carbonyloxy)-8-Methyl-Benzopyran-2-one (Compound 69)

1. A mixture of N-methyl-pyrrole-2-carboxylic acid (4 g) and thionyl chloride (20 ml) in ether (20 ml) was refluxed for 25 mins, and was then evaporated and azeotroped with benzene. The resulting acid chloride was dissolved in methylene chloride (20 ml) and the solution was added with stirring to a solution of N-methyl-pyrrole-2-carboxylic acid) (4.0 gm) in methylene chloride (20 ml) containing pyridine (2.6 ml). The reaction was stirred at room temperature and filtered through a short column of silica gel (30 gm) using methylene chloride as the eluant. The eluants were evaporated to dryness to afford the anhydride.

2. A suspension of 4-amino-7-hydroxy-8-methyl-benzopyran-2-one (4.8 gm) (JACS, 80,140, 1958) in DMF (40 ml) containing triethylamine (3.7 ml) was stirred at 80° C. until homogeneous. To this solution was then added the anhydride from step 1, in DMF (15 ml). The reaction mixture was maintained at that temperature for 12 hours and was then cooled to 0° C. and the solid product was filtered off and washed with cold DMF. The solid was then dissolved in hot DMF (100 ml), treated with charcoal and filtered. The light yellow filtrate was diluted with water and the precipitated title compound was isolated by filtration followed by drying in vacuum (4.1 gm). MS: m/e 298 (M.$^+$).

Example 23

4-Amino-7-Acetyloxy-8-Methyl-Benzopyran-2-one (Compound 68)

Was obtained by using acetic anhydride in step 2 of Example 22. MS (FAB): m/e 276 (M.$^+$+1).

Example 24

4-Amino-7-(2-Furoyloxy)-8-Methyl-Benzopyran-2-one (Compound 65)

Was obtained from 2-furoic acid and 4-amino-7-hydroxy-8-methyl-benzopyran-2-one using the procedure described in Example 22. MS: m/e 285 (M.$^+$).

Example 25

4-Amino-7-(Thiophene-2-carbonyloxy)-8-Methyl-Benzopyran-2-one (Compound 66)

Was obtained from thiophene-2-carboxylic acid and 4-amino-7-hydroxy-8-methyl-benzopyran-2-one using the procedure described in Example 22. MS: m/e 301 (M.$^+$).

Example 26

4-Amino-7-Isonicotinoxy-8-Methyl-Benzopyran-2-one (Compound 67)

Was obtained from isonicotinic acid and 4-amino-7-hydroxy-8-methyl-benzopyran-2-one using the procedure described in Example 22. MS: m/e 296 (M.$^+$).

Example 27

4-Amino-7-(Pyrrol-2-carbonyloxy)-8-Methyl-Benzopyran-2-one (Compound 70)

A solution of pyrrole-2-carboxylic acid chloride (0.065 gm) in methylene chloride (0.5 ml) was added to a suspension of 4-amino-7-hydroxy-8-methyl-benzopyran-2-one (0.095 gm) in pyridine (2 ml). The suspension was heated at 70 for 10 mins. to obtain a homogeneous solution. The reaction mixture was then diluted with water, filtered and the solid was crystallized form dimethylformamide/water to afford the title compound. MS: m/e 284 (M.$^+$).

Example 28

4-Amino-7-(BOC-L-Alanyloxy)-8-Methyl-Benzopyran-2-one (Compound 71)

A solution of dicyclohexylcarbodiimide (0.54gm) in methylene chloride (5 ml) was added dropwise to a solution of Boc-L-alanine (0.99 gm) in methylene chloride (15 ml). The reaction mixture was stirred for 2 hours, filtered and the filtrate was evaporated. The resulting Boc-L-alanine anhydride was dissolved in DMF (10 ml) and added to 4-amino-7-hydroxy-8-methyl-benzopyran-2-one (0.5 gm) followed by the addition of triethylamine (0.37 ml). The solution was then heated at 70° C. for 8 hours and evaporated under reduced pressure. The solid was suspended in methylene chloride-methanol filtered and crystallized from DMF-water to afford the title compound (0.35 gm). MS (FAB): m/e 363 (M$^+$+1).

Example 29

Preparation of 1-Benzyl-3-Formyl-4-Methoxy-6-Methyl-2(1H)-Quinolinone (Formula 1.20)

A solution of 1-benzyl-3-ethoxycarbonyl-4-hydroxy-6-methyl-2(1H)-quinolinone (12.4 g, obtained in step 3 of Preparation A) in dichloromethane (50 ml) and methanol (10 ml) was treated with excess diazomethane in ether for 10 mins and was then evaporated. The crude methylation product upon chromatography on silica gel yielded 1-benzyl-3-ethoxycarbonyl-4-methoxy-6-methyl-2(1H)-quinolinone (11.5 g). This last product (7.13 g) in dry toluene (80 ml) was cooled to −78° C. and a 1M solution of di-isobutyl aluminum hydride (30 ml) was added dropwise in 10 min. After 2.5 hours of stirring at −78° C., the reaction mixture was worked up by stirring with aqueous ammonium chloride/1N hydrochloric acid followed by extraction with methylene chloride. The crude reduction product was chromatographed on silica gel and crystallized from ethyl acetate/hexane to give 1-benzyl-3-formyl-4-methoxy-6-methyl-2(1H)-quinolinone as a yellow solid (7.8 g). That the expected product was obtained was confirmed by the spectral data: NMR (CDCl$_3$): δ2.40 (s, 3H, CH$_3$), 4.18 (s, 3H, OCH$_3$), 10.58 (s, 1H, CHO); MS (FAB): m/e 308 (M$^+$.+1).

Example 30

Preparation of 1-Benzyl-3-Formyl-4-Methoxy-2(1H)-Quinolinone (Formula 1.21)

Following the procedure set forth in Steps (2) and (3) of Preparation A, and using isatoic anhydride, 1-benzyl-3-ethoxycarbonyl-4-hydroxy-2(1H)-quinolinone was obtained. Then, following the procedure set forth in Example 29, 1-benzyl-3-ethoxycarbonyl-4-hydroxy-2(1H)-quinolinone was converted to 1-benzyl-3-formyl-4-methoxy-2(1H)-quinolinone. That the expected product was obtained was confirmed by the spectral data: MS: m/e 293 (M.$^+$); NMR (CDCl$_3$): δ4.20 (s, 3H, OCH$_3$), 10.50 (s, 1H, CHO).

Example 31

Preparation of 1-Heptyl-3-Acetyl-4-Methoxy-2(1H)-Quinolinone (Formula 1.22)

Step (1): Preparation of 1-Heptyl-3-Ethoxycarbonyl-4-Methoxy-2(1H)-Quinolinone

Following the procedure set forth in Preparation A, steps (2–3), isatoic anhydride was converted to 1-heptyl-4-hydroxy-3-ethoxycarbonyl-2(1H)-quinolinone, which upon reaction with excess diazomethane in ether gave the title compound. That the expected product was obtained was confirmed by the spectral data: MS: m/e 345 (M.$^+$).

Step (2): Preparation of 1-Heptyl-3-Acetyl-4-Methoxy-2(1H)-Quinolinone

A flame-dried 50 ml round bottomed flask was charged with copper (I) iodide (909 mg, 4.78 mmole) and anhydrous THF (20 mL). Methyl lithium (halide-free, 1.4M, 7.2 mL, 10.1 mmole) was added to the white CuI suspension at −78° C. After 0.5 hour the product from step (1) (430 mg. 1.25 mmole) was added drop-wise as a solution in THF (10 mL) to the solution of dimethyllithiocuprate. After 3 hours, the reaction was quenched with saturated ammonium chloride. The product was isolated by acidification of the reaction to pH 5, and extraction (3X) with ethyl acetate. Final purification on Silica-Gel 60 (4:1 hexane:ethyl acetate eluent) gave the title compound in 75% yield. That the expected product was obtained was confirmed by the spectral data: M.S. (E.I.): 315 (M.$^+$); NMR (CDCl$_3$): δ8.0 (1H, d), 7.6 (1H, dd), 7.35 (1H, dd), 7.2 (1H, dd), 4.25 (2H, m, CH$_2$N), 3.98 (3H, s, OCH$_3$),2.65 (3H, s, C(O)CH$_3$), 1.8 (2H, m), 1.35 (8H, m), 0.9 (3H, t, CH$_3$).

Example 32

Preparation of 1-Hexyl-3-Formyl-4-Methoxy-6-Methyl-2(1H)-Quinolinone (Formula 1.28)

Using hexyl bromide instead of benzyl bromide and following steps (1–3) in Preparation A, 1-hexyl-3- ethoxycarbonyl-4-hydroxy-2(1H)-quinolinone was obtained. Then, following the procedure set forth in Example 29, the 1-hexyl-3-ethoxycarbonyl-4-hydroxy-2 (1H)-quinolinone was converted to the title compound. That the expected product was obtained was confirmed by the spectral data: MS: m/e 301 (M.$^+$); NMR (CDCl$_3$): δ4.15 (s, 3H, OCH$_3$), 10.56 (s, 1H, CHO).

Example 33

Preparation of 1-Hexyl-3-Formyl-4-Methoxy-2(1H)-Quinolinone (Formula 1.26)

Following steps (2–3) in Preparation A, and using hexyl bromide and isatoic anhydride, 1-hexyl-3-ethoxycarbonyl-4-hydroxy-2(1H)-quinolinone was obtained. Then, following the procedure set forth in Example 29, the 1-hexyl-3-ethoxycarbonyl-4-hydroxy-2(1H)-quinolinone was converted to the title compound. That the expected product was obtained was confirmed by the spectral data: MS (FAB): m/e 287 (M.$^+$); NMR (CDCl$_3$): δ4.15 (s, 3H, OCH$_3$), 10.52 (s, 1H, CHO).

Example 34

Preparation of 1-Methyl-3-Formyl-4-Methoxy-2 (1H)-Quinolinone (Formula 1.27)

Starting with 1-methyl-3-ethoxycarbonyl-4-hydroxy-2 (1H)-quinolinone (J. Org. Chem. 829 (1976), the disclosure of which is incorporated herein by reference thereto) and following the procedure set forth in Example 29, the title compound was obtained. That the expected product was obtained was confirmed by the spectral data: MS (EI): m/e 217 (M.$^+$); NMR (CDCl$_3$): δ3.70 (s, 3H, NHCH$_3$), 4.15 (s, 3H, OCH$_3$), 10.50 (s, 1H, CHO).

Biological Data

Cell and Virus Culture

HeLa and Vero cell cultures were maintained in Eagles Minimal Essential Medium (EMEM) which was supplemented with glutamine, penicillin, streptomycin and 10% fetal calf serum (10% EMEM). Stock cultures of HSV-2 (strain MS available from ATCC VR-540) were grown in and harvested from Vero cells. Viral stocks were titered in Vero cells according to established procedures.

Plasmid Constructions

Plasmid pON 245$^{ori-}$ contains the promoter of the HSV-1 thymidine kinase (tk) gene located immediately 5'of the *E. coli* lac Z gene. In this arrangement, the tk promoter controls transcription from the bacterial gene in transient expression assays. Additionally, an SV40 polyadenylation signal is present at the 3' end of the lac Z gene to allow for the efficient translation of the mRNA in eucaryotic cells. The expression of beta galactosidase in a transient assay using pON 245$^{ori-}$ is dependent upon superinfection of the transfected cells with HSV. Therefore, a compound which interferes with early steps of HSV replication will also inhibit beta-galactosidase production in transfected cells. For example see U.S. application Ser. No. 07/435,491 filed Sep. 5, 1989, the disclosure of which is incorporated herein by reference thereto.

Transient Expression of Beta Galactosidase in Transfected Cells

HeLa cells were seeded into 96 well microtiter plates and allowed to grow to 80% confluency (approximately 35000 cells/well). One half microgram of plasmid pON 245$^{ori-}$ DNA was introduced into the cells of each well by the DEAE Dextran precipitation technique (Grahman and Van der Eb, 1973). Four to six hours later, the cells were rinsed with hank's Balanced Salt Solution (HBSS), overlaid with 10% EMEM and incubated at 37° C. At 24 hours post-transfection, cells were rinsed, overlaid with 10% EMEM again and re-incubated at 37° C. At 48 hours post-transfection, cells were rinsed and overlaid with either EMEM containing 2% fetal calf serum (2% EMEM), 2% EMEM containing HSV-2 (strain MS, Multiplicity of Infection [moi]=5 pfu/cell) or 2% EMEM containing HSV-2 and the appropriate concentration of Schering compound to be tested. Twenty-four hours later, the cells were harvested and assayed for beta galactosidase activity as described below.

Beta Galactosidase Assay

All determinations of beta galactosidase activity were performed in 96 well microtiter plates. The intracellular level of beta galactosidase activity in each well was determined from cell lysates of the monolayer cultures. Aliquots were assayed by incubation in the presence of beta galactosidase substrate, 4-methylumbelliferyl-β-D-galactoside (MUG, 125 ug/ml, Sigma), for 2 hours. The generation of fluorescent product was quantified on a Microfluor microfluorimeter (Dynatech) after addition of 0.1M glycine, pH 10.3 (Spaete and Mocarski, 1985). The inhibitory activity of a compound was plotted versus the concentration and an IC50 value (the concentration of compound required to reduce beta glactosidase expression by 50%) was obtained for each compound tested.

Compound Toxicity Assay

Compounds which demonstrated a significant inhibitory activity in the HeLa cell beta galactosidase assay were assayed for their inhibitory effect on HeLa cell translation. HeLa cells were treated with inhibitory compound for 24 hours, after which levels of translational activity were assayed.

For assay of translational activity, HeLa cultures were grown to 80% confluency in 96 well microtiter plates, treated with appropriate concentrations of compound in 2% EMEM during an overnight incubation at 37° C., then rinsed with HBSS and overlaid with 0.8 ml of 2% EMEM containing 8 uCi of tritiated leucine ($^3$H-LEU, 141 Cu/mMol, Amersham Corp., Arlington Heights, Ill.). After a 1 hour incubation at 36.5° C., the cells were rinsed twice with phosphate buffered saline (PBS) and lysed in 400 ul/well of 1×PBS, 0.5% sodium dodecyl sulphate (SDS). After a 10 min incubation at 36.5° C., the contents of the well were transferred to a well in a Millititer HA microfiltration plate (Millipore Corp., Bedford, Mass.). The TCA insoluble proteins were precipitated onto the filter disc by a 10 min fixation with 5% TCA, followed by filtration under vacuum and three 10 minute rinses with 95% ethanol. The filters were dried at room temperature, cut from the milltitier plate and transferred to scintillation vials. TCA precipitable counts were assayed in 5 ml of Scintisol (Isolab, Akron, Ohio). The inhibitory activity of a compound was plotted versus the concentration and an IC50 value (that concentration of the compound required to decrease cellular translational activity by 50%) was derived for each compound.

Analysis of In Vivo Efficacy

The in vivo assessment of anti-HSV efficacy was determined in the prophylactic guinea pig model of HSV infection described by Stansberry et al (1982). Dosing of guinea pigs comprised an initial treatment with test compound given 24 hours prior to virus infection and subsequent administration of the compound every eight hours (T.I.D.) for a total of 10 days. Test compounds were administered subcutaneously in 0.5% buffered methyl celluslose at a dose of 60 mg per kg body weight of the animal. Animals were monitored daily for the development of genital lesions and neurological symptomology, both of which were recorded and compared to the results obtained with parallel groups which received placebo or acyclovir treatment. Efficacy was evaluated for each compound by scoring the ability of the compound to ameliorate genital lesions produced by infection with HSV-2, strain MS, expressed as Maximum Lesion Scores (MLS) on a scale of 1 (least lesions) to 4 (severe lesions).

IN VITRO ANTI-HSV ACTIVITY

The in vitro anti-HSV activity of compounds of this invention is set forth in Table II.

TABLE II

| COMPOUND NO. (IN TABLE I) | ANTI-HSV ACTIVITY HSV-β-GAL ASSAY IC$_{50}$ (μg/ml) | CYTOTOXICITY $^3$H-LEU ASSAY IC$_{50}$ (μg/ml) |
| --- | --- | --- |
| 1 | 1.5 | 1.8 |
| 2 | 2 | 32 |
| 3 | 2.5 | 12.6 |
| 4 | 3 | 100 |
| 5 | 3 | 15 |
| 6 | 3 | 7 |
| 7 | 3 | 37 |
| 8 | <3 | 3 |
| 9 | <3 | 25 |
| 10 | 4 | >100 |
| 11 | 4.5 | 17 |
| 12 | 4.5 | 32 |
| 13 | 5 | 17 |
| 14 | 5 | >100 |
| 15 | 5 | 25 |
| 16 | 5 | 18 |
| 17 | 6 | 25 |
| 18 | 6 | 18 |
| 19 | 7 | — |
| 20 | 7 | — |
| 22 | 8 | 25 |
| 23 | 9 | >100 |
| 24 | 10 | — |
| 25 | 10 | — |
| 26 | 7.0 | 27 |

The in-vitro anti-HSV activity of further compounds of the invention is Table II[1]:

TABLE II[1]

| Compound No. | Anti-HSV Activity HSV-β-Gal Assay IC$_{50}$ (μg/ml) | CYTOXICITY $^3$H-LEU Assay IC$_{50}$ (μg/ml) |
| --- | --- | --- |
| 65 | >25.0 | — |
| 66 | >25.0 | — |
| 67 | 14.0 | — |
| 68 | 30.0 | — |
| 69 | 9.8 | 100 |
| 70 | 15.5 | 74 |
| 71 | >25.0 | — |

In Vivo Anti-HSV Activity

The in vivo anti-HSV activity of a compound of this invention is set Table III:

TABLE III

| COMPOUND | MSL[1] | NEUROLOGICAL DYSFUNCTION (%)[2] |
| --- | --- | --- |
| Placebo | 2.22 | 66 |
| Acyclovir | 1.61 | 44 |
| No. 9 (in Table I) | 1.44 | 44 |

[1]Maximum Lesion score on a scale of 1–4.
[2]Percentage animals developing loss of bladder/hindlimb control Certain specific compounds of Formula 1.0 wherein X is nitrogen and which fall within the scope of this invention but which did not provide vitro results are listed in Table IV:

TABLE IV

| No.* | R$^3$ | R | R$^1$ | R$^2$ | HSV(1) |
| --- | --- | --- | --- | --- | --- |
| 101 | CH$_3$ | —C(O)OC$_2$H$_5$ | —OCO—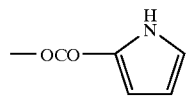 | — | 20 |
| 102 | CH$_3$ | phenylthio | —OC(O)CH$_3$ | 6-F | 21 |

TABLE IV-continued

| No.* | R³ | R | R¹ | R² | HSV(1) |
|---|---|---|---|---|---|
| 103 | $C_6H_{13}$ | —C(O)OC$_2$H$_5$ | —OCO-(N-methylpyrrole) | 6-CH$_3$ | 25 |
| 104 | $C_6H_{13}$ | —C(O)OCH$_2$CH=CH$_2$ | —OCH$_3$ | 6-CH$_3$ | >25 |
| 105 | $C_6H_{13}$ | —CO$_2$Na | —OCH$_3$ | 6-CH$_3$ | >25 |
| 106 | CH$_3$ | —CH$_2$CH$_2$OH | —OCH$_3$ | — | >25 |
| 107 | CH$_3$ | —C(O)OC$_2$H$_5$ | —OCH$_3$ | — | >25 |

(1)HSV: anti-HSV activity, HSV-β-Gal Assay, IC$_{50}$ (μg/ml)
*Further compounds numbered independently of earlier compounds.

In Table IV the "Cytotoxicity $^3$H-Leu Assay IC$_{50}$(μ/ml) result for the compound numbered 101 was 40.

Antihypertensive Activity

I. SHR Analysis

The ability of the compounds to lower blood pressure can be assessed in vivo in conscious spontaneously hypertensive rats (SHR). SHR are purchased from Taconic Farms, Germantown, N.Y. and are approximately 16–18 weeks old when anesthetized with ether. The caudal ventral tail) artery is cannulated with polyethylene tubing (PE50) and blood pressure and heart rate are recorded as described by Baum, T. et. al, J. Cardiovasc. Pharmacol. Vol 5, pp. 665–667, (1983). Rats are placed into pastic cylindrical cages where they rapidly recover consciousness. Blood pressure and heart rate are allowed to stabilize for approximately 90 minutes prior to compound administration. Compounds are administered orally as solutions or suspensions in 0.4% aqueous methylcellulose vehicle via a feeding needle. The compound or 0.4% aqueous methylcellulose vehicle are given in a volume of 4 ml/kg to SHRs that had been fasted overnight. Alternatively, compounds are administered intravenously. The compound is solubilized with a minimum amount of an organic solvent such as ethanol or dimethylsulfoxide and given in physiological saline. Activity is expressed as the fall in mean blood pressure (MBP) in millimeters of mercury (mm Hg). Compound-induced changes are compared with the changes in an appropriate placebo group.

The SHR results are set forth in Table V.

TABLE V

IN-VIVO SHR RESULTS

| COMPOUND NO. (IN TABLE I) | DOSAGE (mpk)$^{(1)}$ | MBP (mm of Hg) |
|---|---|---|
| 27 | 25 (p.o) | 19 |
| 27 | 50 (p.o) | 24 |
| 27 | 100 (p.o) | 59 |

$^{(1)}$mpk: mg per kg of bodyweight

II. Phosphodiesterase inhibition in vitro

Phosphodiesterase enzymes are known to hydrolyze cGMP in smooth muscle. High levels of cGMP are associated with the relaxation of vascular smooth muscle, with a consequent subsequent reduction in blood pressure. Thus, it is believed that by inhibiting these phosphodiesterase enzymes, cGMP levels in muscle will be either maintained or increased with a subsequent reduction in blood pressure. Compounds are evaluated for inhibition of a phosphodiesterase enzyme which hydrolyzes cyclic guanosine monophosphate (cGMP). The enzyme, cGMP phosphodiesterase (cGMP-PDE), is a homogeneous enzyme obtained from bovine lung and purified by ion-exchange chromatography, gel filtration, and sucrose gradient centrifugation. cGMP-PDE is highly selective for cGMP. Bovine aorta homogenates and primary cultures of bovine aortic endothelial and vascular smooth muscle cells contain an enzyme with properties very similar to the lung isozyme.

The enzyme assay is performed using a Biomek Automated Pipetting Station. Compounds are dissolved in distilled water or DMSO and diluted with 10% DMSO. Compounds are tested at several concentrations at log intervals, typically 0.1,1.0,10, and 100 μM final concentration.

Assays contain the following components:

1 μM substrate $^3$H-cGMP 50 mM Tris-HCl, pH 7.5, 5 mM magnesium chloride (MgCl$_2$)

0.5 mg/ml snake venom alkaline phosphatase

Assays are initiated by addition of enzyme and stopped by addition of 10 mM isobutylmethylxanthine, a general phosphodiesterase inhibitor. Assays are performed for 25 minutes at room temperature to achieve 5–10% hydrolysis of substrate. The negatively charged substrates are then separated from guanosine by binding to an anion-exchange resin (AGI-X8) and centrifugation or filtration, and the product is quantitated by scintillation counting in counts.

% Inhibition=100-[(cpm compound-blank)/(cpm control-blank)× 100]

Activity is expressed as the IC$_{50}$ value, to inhibit activity of the enzyme by 50 per cent. The cGMP-PDE IC$_{50}$ results are set forth in Table VI.

TABLE VI

IN-VITRO cGMP-PDE RESULTS

| COMPOUND NO. (IN TABLE I) | cGMP-PDE IC$_{50}$ (μM) |
|---|---|
| 9 | 6.0 |
| 27 | 4.0 |
| 28 | 3.0 |

A specific compound of Formula 1.0 wherein X is NR$^3$ and which falls within the scope of the antihypertensive compounds of this invention but which did not provide optimum activity in the SHR and/or the in-vitro cGMP-PDE inhibition assays is listed in Table VII:

TABLE VII

| R³ | R | R¹ | R² | cGMP-PDE IC$_{50}$ ($\mu$M) | MBP (mm Hg) |
|---|---|---|---|---|---|
| Bzl[1] | —CO$_2$C$_2$H$_5$ | —OCH$_3$ | 6-CH$_3$ | 8.0 | 0[5] |

[1]Compound No. 7 of Table I.
[2]at 25 mpk (P.O.).

The invention having been thus described, it will be obvious that it may be varied in many ways. Such variations are not to be regarded as a departure from the spirit and scope of the invention and all such modifications are included within the scope of the claims.

We claim:

1. A compound of the formula:

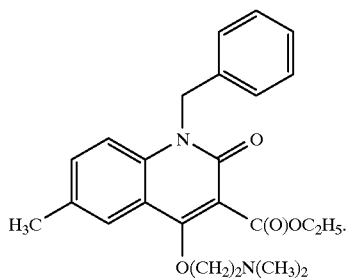

2. A compound of the formula:

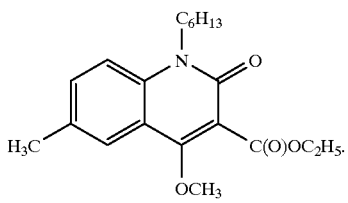

3. A compound of the formula:

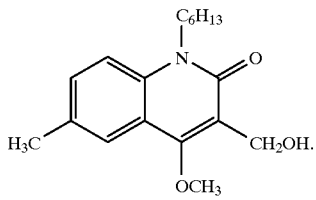

4. A pharmaceutical composition comprising an effective amount of a compound of claim 1 together with a pharmaceutically acceptable carrier.

5. A pharmaceutical composition comprising an effective amount of a compound of claim 2 together with a pharmaceutically acceptable carrier.

6. A pharmaceutical composition comprising an effective amount of compound of claim 3 together with a pharmaceutically acceptable carrier.

7. A method of treating a patient suffering from hypertension comprising administering to such patient and effective antihypertensive amount of a compound of claim 1.

8. A method of treating a patient suffering from hypertension comprising administering to such patient an effective antihypertensive amount of a compound of claim 2.

* * * * *